(12) United States Patent
Zhang et al.

(10) Patent No.: US 12,357,321 B2
(45) Date of Patent: Jul. 15, 2025

(54) OSTEOTOMY GUIDE

(71) Applicant: DePuy Synthes Products, Inc., Raynham, MA (US)

(72) Inventors: Mingjun Zhang, Jiangsu (CN); Qiang Xu, Jiangsu (CN); Wenhao Qi, Jiangsu (CN); Weiwei Xiang, Jiangsu (CN); Xiaolong Wang, Jiangsu (CN)

(73) Assignee: DePuy Synthes Products, Inc., Raynham, MA (US)

( * ) Notice: Subject to any disclaimer, the term of this patent is extended or adjusted under 35 U.S.C. 154(b) by 469 days.

(21) Appl. No.: 17/602,443

(22) PCT Filed: Aug. 23, 2019

(86) PCT No.: PCT/CN2019/102153
§ 371 (c)(1),
(2) Date: Oct. 8, 2021

(87) PCT Pub. No.: WO2020/206902
PCT Pub. Date: Oct. 15, 2020

(65) Prior Publication Data
US 2022/0211388 A1    Jul. 7, 2022

(30) Foreign Application Priority Data

Apr. 12, 2019   (WO) ............... PCT/CN2019/082425

(51) Int. Cl.
*A61B 17/15*   (2006.01)
*A61B 17/17*   (2006.01)

(52) U.S. Cl.
CPC .......... *A61B 17/151* (2013.01); *A61B 17/155* (2013.01); *A61B 17/157* (2013.01); *A61B 17/1764* (2013.01)

(58) Field of Classification Search
CPC ... A61B 17/151; A61B 17/155; A61B 17/157; A61B 17/1764
(Continued)

(56) References Cited

U.S. PATENT DOCUMENTS 5,423,827 A  *  6/1995  Mumme ............ A61B 17/1764
                                                408/115 R
8,083,746 B2   12/2011  Novak
(Continued)

FOREIGN PATENT DOCUMENTS

CN    104736072 A    6/2015
CN    104825214 A    8/2015
(Continued)

*Primary Examiner* — Jessica Weiss
(74) *Attorney, Agent, or Firm* — BakerHostetler

(57) ABSTRACT

An osteotomy guide (100,500,600) guides cutting of a bone (300). The guide (100,500,600) has an anterior end (106,506,606) and a posterior end (108,508,608) that are spaced from one another along a transverse direction. The guide (100,500,600) has an inner surface (102,502,602) that faces the bone (300), and an outer surface (104,504,604) opposite the inner surface (102,502,602) along an outer direction ($D_o$). The guide (100,500,600) includes a transverse guide surface (138,538,638) that extends along a transverse axis ($A_T$) along the transverse direction so as to define a transverse cutting path into the bone (300). The guide (100,500,600) includes an ascending guide surface (134,534,634) that extends along an ascending axis ($A_A$) along an ascending direction so as to define an ascending cutting path into the bone (300). The transverse and ascending axes ($A_T, A_A$) intersect one another.

18 Claims, 23 Drawing Sheets

(58) Field of Classification Search
USPC .................................................. 606/79, 87
See application file for complete search history.

(56) References Cited

U.S. PATENT DOCUMENTS

| | | | | |
|---|---|---|---|---|
| 8,377,068 B2* | 2/2013 | Aker | ............... | A61B 17/157 606/88 |
| 11,399,849 B2 | 8/2022 | Podgorski et al. | | |
| 2006/0155291 A1 | 7/2006 | Farrar et al. | | |
| 2006/0241636 A1 | 10/2006 | Novak et al. | | |
| 2008/0015605 A1* | 1/2008 | Collazo | ............ | A61B 17/157 606/87 |
| 2009/0087276 A1 | 4/2009 | Rose | | |
| 2009/0088755 A1* | 4/2009 | Aker | ............... | A61B 17/157 606/79 |
| 2012/0143199 A1 | 6/2012 | Young | | |
| 2014/0066720 A1* | 3/2014 | Wilkinson | ......... | A61B 17/02 606/88 |
| 2015/0305752 A1 | 10/2015 | Eash | | |
| 2016/0287298 A1 | 10/2016 | Pavlov et al. | | |
| 2017/0325826 A1 | 11/2017 | Bake et al. | | |
| 2017/0360453 A1 | 12/2017 | Brailovski et al. | | |
| 2018/0049749 A1 | 2/2018 | Wu et al. | | |
| 2019/0150943 A1 | 5/2019 | Wu et al. | | |
| 2019/0314038 A1 | 10/2019 | Maxson | | |

FOREIGN PATENT DOCUMENTS

| | | |
|---|---|---|
| CN | 104825215 A | 8/2015 |
| CN | 105193475 A | 12/2015 |
| CN | 205339051 U | 6/2016 |
| CN | 205359552 U | 7/2016 |
| CN | 206333941 U | 7/2017 |
| CN | 107072672 A | 8/2017 |
| CN | 107320153 A | 11/2017 |
| CN | 107753088 A | 3/2018 |
| CN | 207532417 U | 6/2018 |
| CN | 108618823 A | 10/2018 |
| CN | 109512484 A | 3/2019 |
| EP | 1444957 A1 | 8/2004 |
| JP | 06-014947 A | 1/1994 |
| JP | 2005-535426 A | 11/2005 |
| JP | 2008-529607 A | 8/2008 |
| JP | 2010-540123 A | 12/2010 |
| JP | 2016-093736 A | 5/2016 |
| JP | 2018-115316 A | 7/2018 |
| JP | 2019-034120 A | 3/2019 |
| JP | 2019-202108 A | 11/2019 |
| TW | I655926 B | 4/2019 |
| WO | 2015/061917 A1 | 5/2015 |
| WO | 2019/033551 A1 | 2/2019 |
| WO | 2019/038240 A1 | 2/2019 |

* cited by examiner

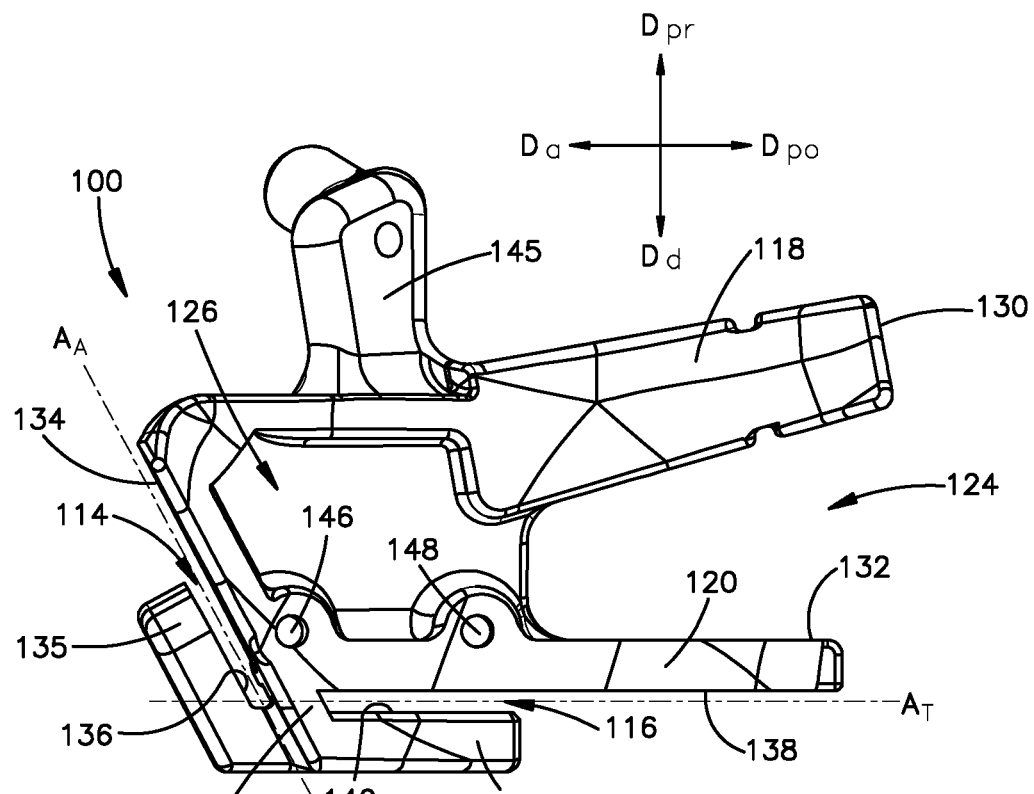

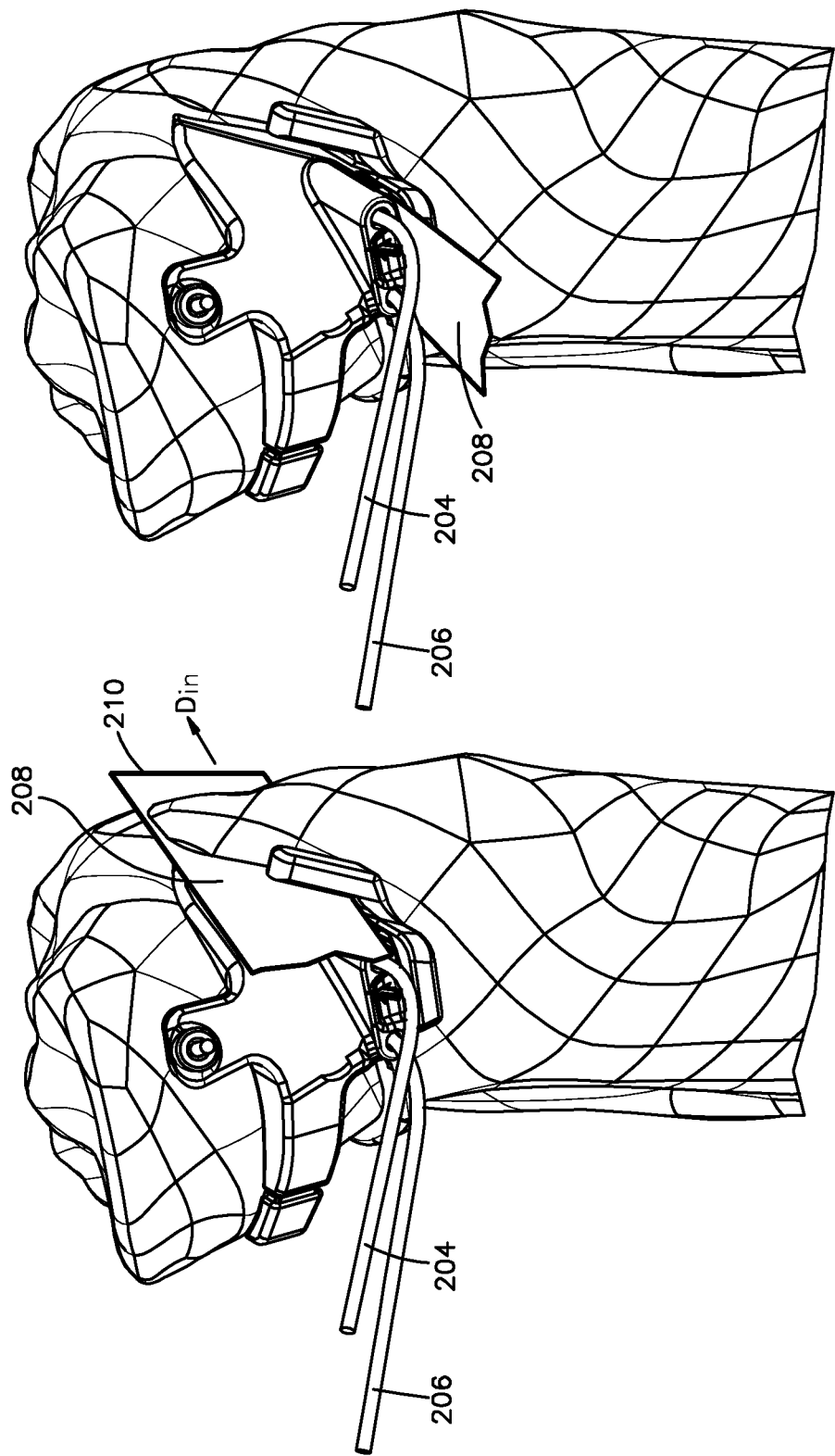

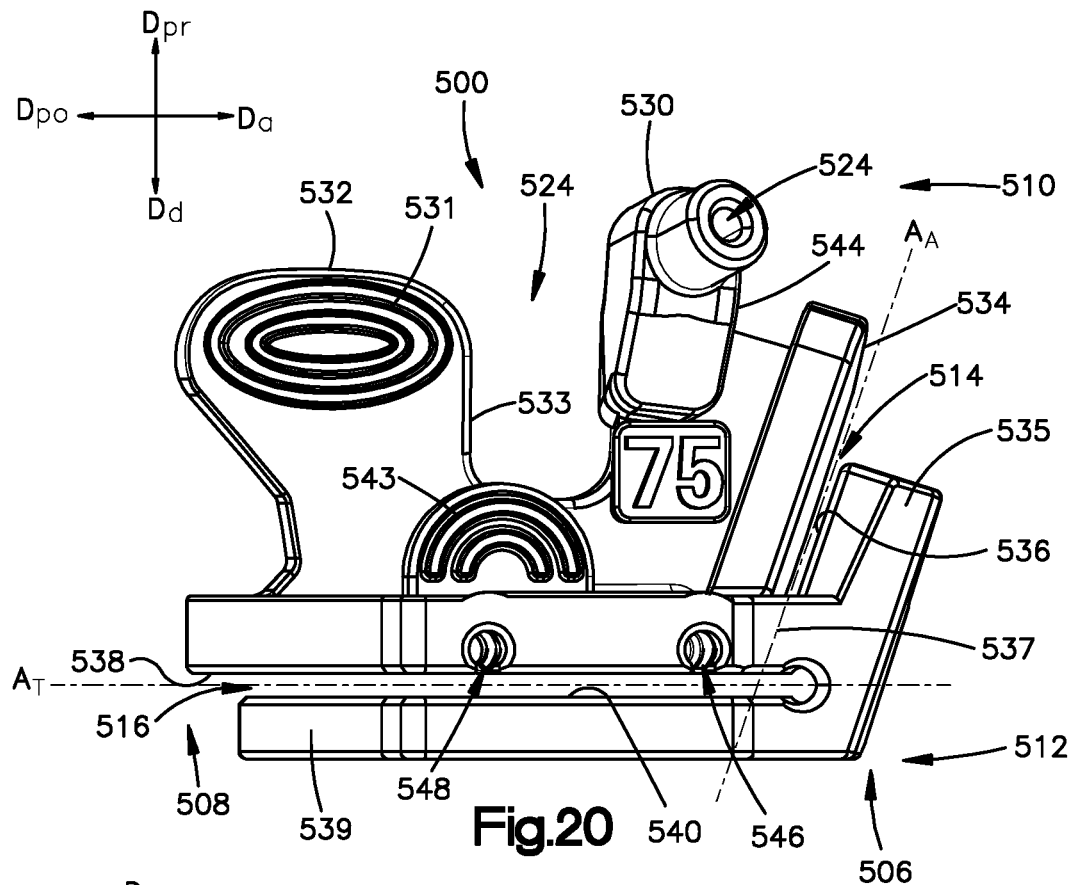
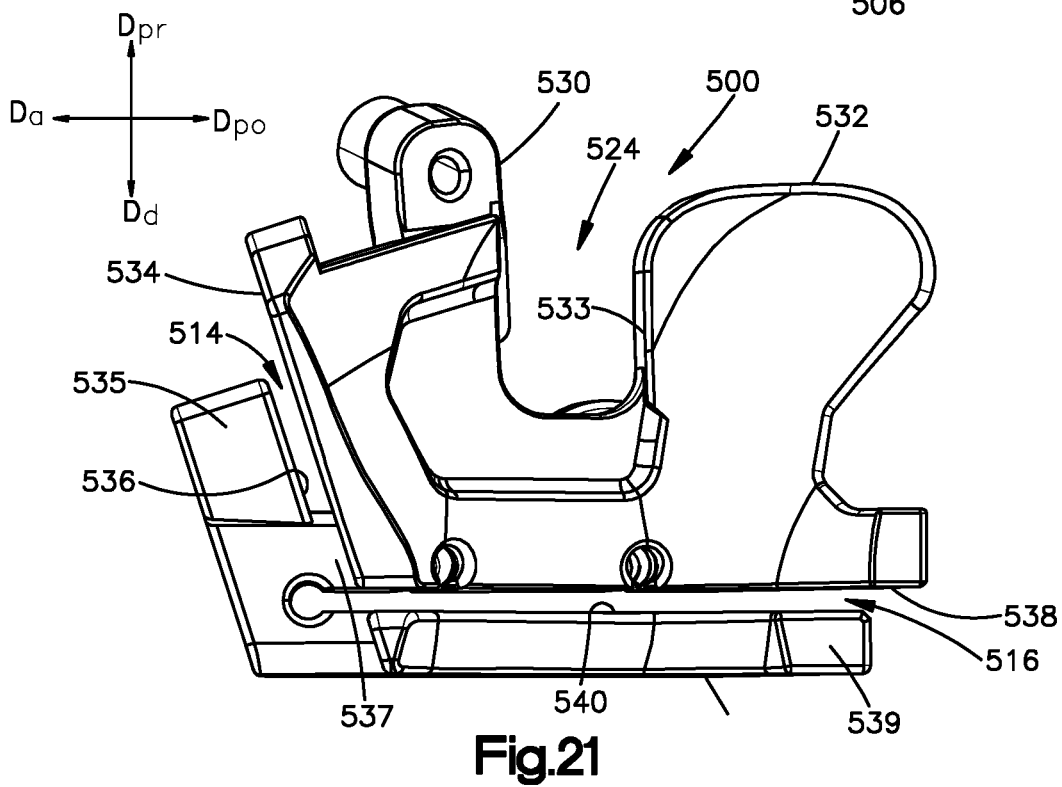

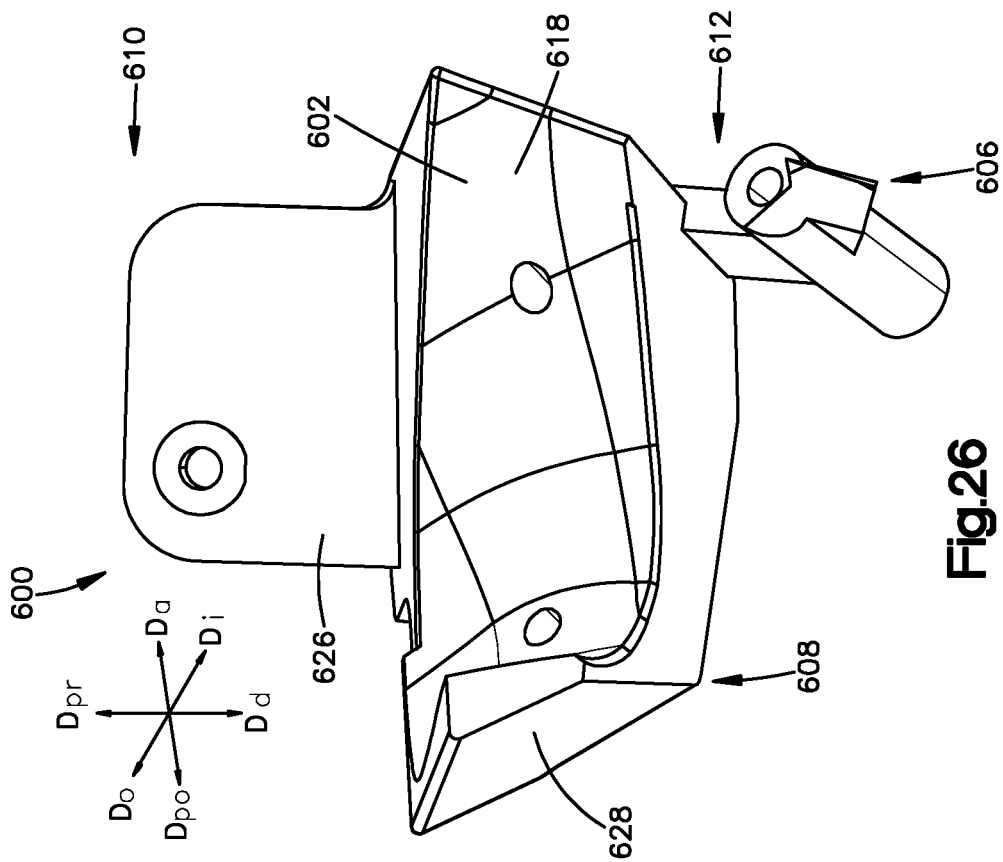
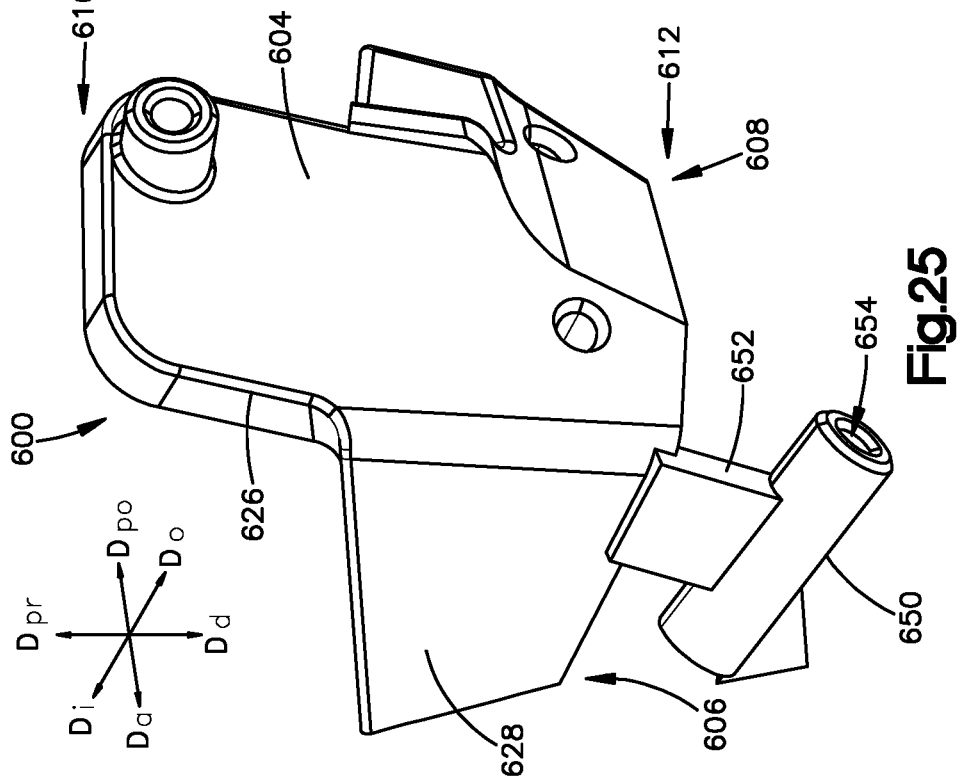

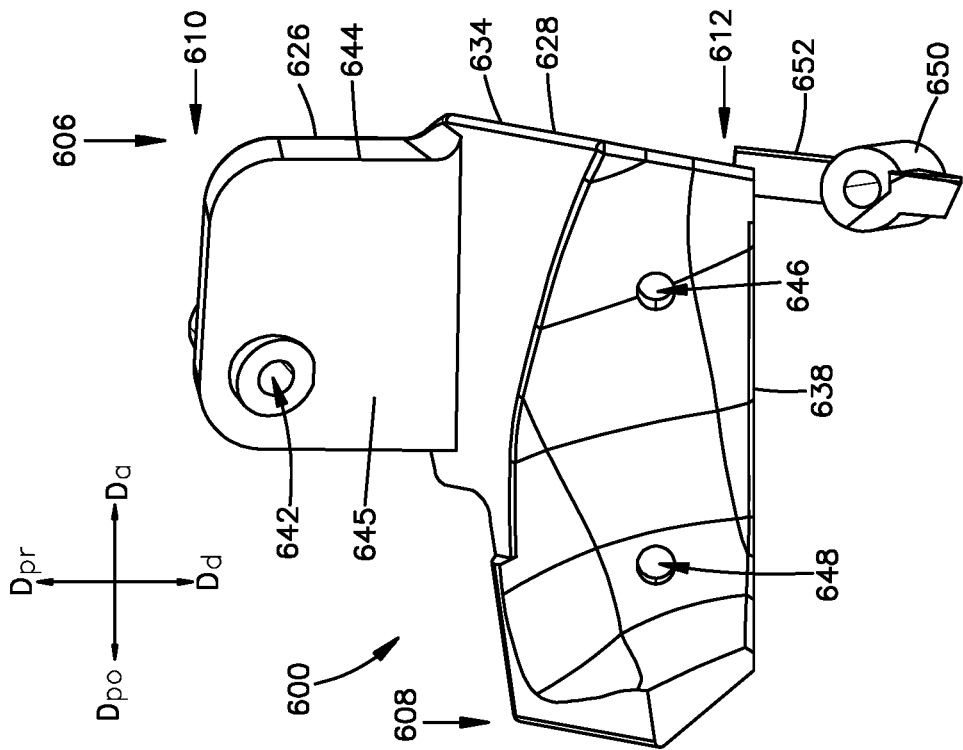
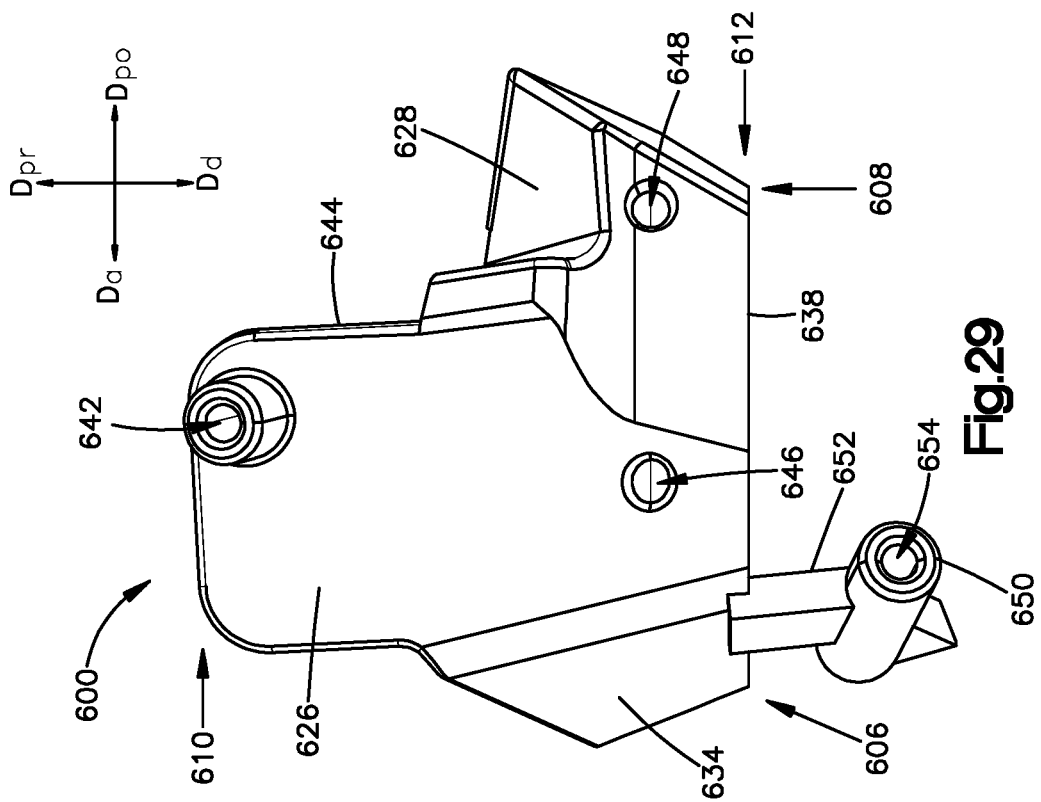

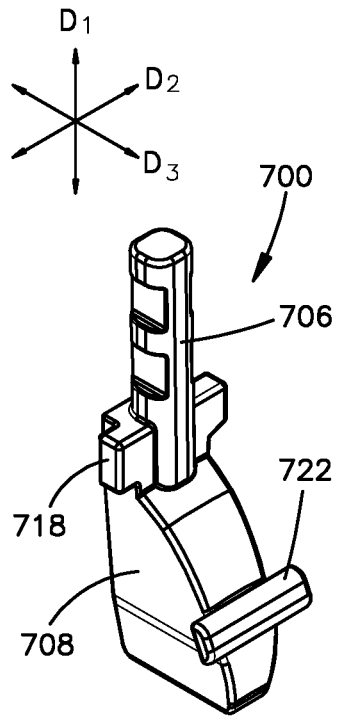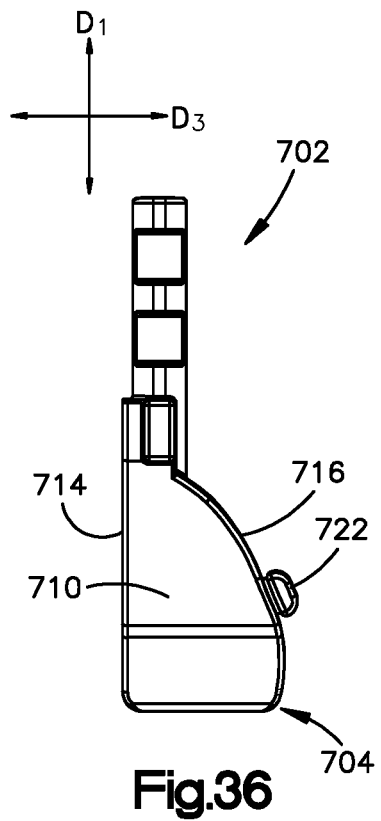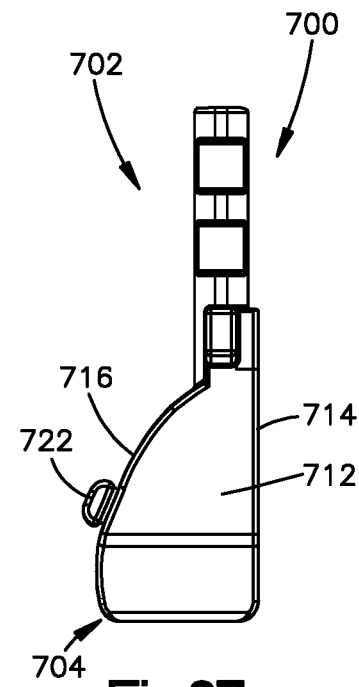
Fig.35  Fig.36  Fig.37
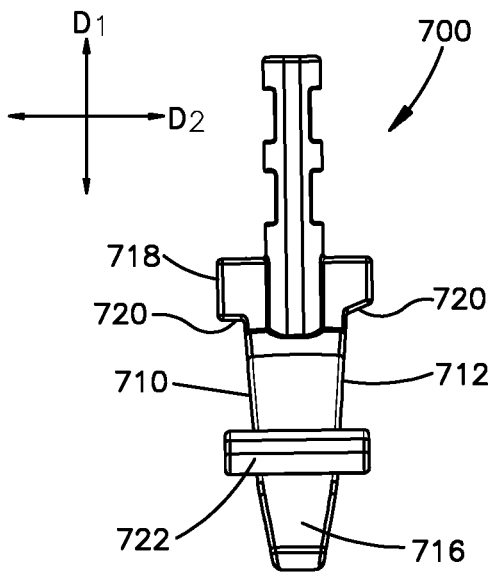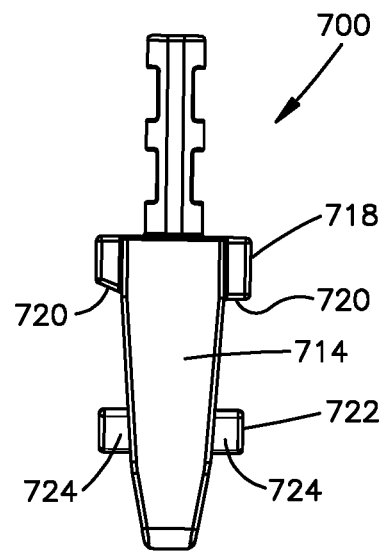
Fig.38  Fig.39

OSTEOTOMY GUIDE

CROSS-REFERENCE TO RELATED APPLICATIONS

This application is the National Stage of International Patent Application No. PCT/CN2019/102153, filed Aug. 23, 2019, which claims the benefit of International Application No. PCT/CN2019/082425, filed Apr. 12, 2019, the disclosures of which are incorporated herein by reference in their entireties.

TECHNICAL FIELD

The present disclosure relates to a surgical guide for cutting bone during an osteotomy, and methods for using the same.

BACKGROUND

The cartilage in a joint, such as a knee, can wear down over time or become damaged due to an injury related to physical activity, resulting in osteoarthritis. Wearing of the cartilage can result in pain that limits the activity of daily life. Typically, osteoarthritis was treated by implanting an artificial joint to replace the original joint. However, there are several drawbacks to full joint replacements. For instance, joint replacements often require large portions of the articular surface of the joint to be removed to accommodate fixation of a metal or polymer joint implant. Further, replacement joints often have a limited life of up to twenty years, and therefore, subsequent replacement surgeries are often needed. Yet further, joint replacements are often complicated by postoperative infection, osteolysis, and osteoporosis, which may require an additional surgery.

Some patients with early onset of osteoarthritis experience cartilage wear of only a portion of the articular surface, such as cartilage wear of less than all of the compartments of the joint. For example, some patients may experience bi-compartmental osteoarthritis of two compartments of the joint or uni-compartmental osteoarthritis of a single compartment of the joint. For patients with compartmental osteoarthritis, it might not be necessary to remove and replace the entire articular surface. Therefore, an osteotomy, such as a high tibial osteotomy, can be performed in patients with limited cartilage wear. For example, a medial high-tibial osteotomy can be performed for patients with medial compartmental osteoarthritis to realign the knee joint.

A medial high-tibial osteotomy is performed by making a cut into the patient's tibia at a location that is adjacent the proximal end of the tibia and on the medial side. The proximal end of the patient's tibia is pivoted to enlarge the cut so as to realign the weight bearing line, to balance the pressure in the knee. The proximal end of the tibia can then be fixed in position so as to maintain the enlarged cut by attaching a bone plate to the tibia. The bone plate extends across the enlarged cut and is attached to the tibia on opposed sides of the cut. In some procedures, the cut can be filled with bone graft or artificial bone before or after the plate is attached.

SUMMARY

In an example embodiment, an osteotomy guide is configured to guide cutting of a bone. The guide comprises an anterior end and a posterior end that are spaced from one another along a transverse direction. The guide comprises an inner surface configured to face bone, and an outer surface opposite the inner surface along an outer direction. Each of the inner surface and the outer surface extends between the anterior end and the posterior end. The inner surface defines i) a first bone contacting region, and ii) a second bone contacting region that is spaced from the first bone contacting region so as to define a gap therebetween. The gap extends from the first bone contacting region to the second bone contacting region, and extends from the inner surface toward the outer surface along the outer direction. The osteotomy guide comprises at least one transverse guide surface that extends between the outer surface and the inner surface, and is oriented along a transverse axis along the transverse direction so as to at least partially define a transverse cutting path into the bone. The at least one transverse guide surface is offset from the gap along a distal direction. The osteotomy guide comprises at least one ascending guide surface that extends between the outer surface and the inner surface. The ascending guide is oriented along an ascending axis along an ascending direction so as to at least partially define an ascending cutting path into the bone. The ascending direction is angularly offset from the distal direction and the transverse direction, and the ascending axis and transverse axis intersect one another.

In another embodiment, an osteotomy guide is configured to guide cutting of a bone. The osteotomy guide comprises an anterior end and a posterior end that are spaced from one another along a transverse direction. The osteotomy guide comprises an inner surface configured to face the bone, and an outer surface that is opposite the inner surface. At least a portion of the inner surface is contoured to face the bone. The osteotomy guide comprises first and second transverse guide surfaces that face each other so as to define a transverse groove therebetween that extends along a transverse axis along the transverse direction so as to define a transverse cutting path. The osteotomy guide comprises first and second ascending guide surfaces that face each other so as to define an ascending groove therebetween that extends along an ascending axis along an ascending direction, wherein the ascending axis and transverse axis intersect one another.

In yet another embodiment, an osteotomy guide is configured to guide cutting of a bone. The osteotomy guide comprises an anterior end and a posterior end that are spaced from one another along a transverse direction. The osteotomy guide comprises an inner surface configured to face bone, and an outer surface opposite the inner surface along an outer direction. Each of the inner surface and the outer surface extends between a posterior end of the osteotomy guide and an anterior end of the osteotomy guide. The inner surface defines i) a first bone contacting region, ii) a second bone contacting region that is spaced from the first bone contacting region so as to define a gap therebetween that extends from the inner surface towards the outer surface along the outer direction, and iii) a third bone contacting region that extends between the first bone contacting region and the second bone contacting region and at least partially defines the gap. The osteotomy guide comprises at least one transverse guide surface that extends between the outer surface and the inner surface, and is oriented along a transverse axis along the transverse direction so as to at least partially define a transverse cutting path into the bone. The osteotomy guide comprises at least one ascending guide surface that extends between the outer surface and the inner surface, and is oriented along an ascending axis along an ascending direction so as to at least partially define an ascending cutting path into the bone. The ascending axis and transverse axis intersect one another.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 5 shows elevation view of an inner side of the osteotomy guide of FIG. 1;

FIG. 6 shows elevation view of an outer side of the osteotomy guide of FIG. 1;

FIG. 13 shows a perspective view of the tibia, fibula, and osteotomy guide of FIG. 10 with a cutting instrument making an ascending cut in the bone;

FIG. 14 shows a perspective view of the tibia, fibula, and osteotomy guide of FIG. 10 with a cutting instrument making a transverse cut in the bone;

FIG. 20 shows elevation view of an outer side of the osteotomy guide of FIG. 16;

FIG. 21 shows elevation view of an inner side of the osteotomy guide of FIG. 16;

FIG. 25 shows an outer perspective view of an osteotomy guide according to yet another embodiment;

FIG. 26 shows an inner perspective view of the osteotomy guide of FIG. 25;

FIG. 29 shows elevation view of an outer side of the osteotomy guide of FIG. 25;

FIG. 30 shows elevation view of an inner side of the osteotomy guide of FIG. 25;

FIG. 35 shows a perspective view of a spacer according to one embodiment;

FIG. 36 shows an elevation view of one side of the spacer of FIG. 35;

FIG. 37 shows an elevation view of another side of the spacer of FIG. 35;

FIG. 38 shows an elevation view of a front end of the spacer of FIG. 35;

FIG. 39 shows an elevation view of a rear end of the spacer of FIG. 35;

DETAILED DESCRIPTION OF ILLUSTRATIVE EMBODIMENTS

Figure 1:
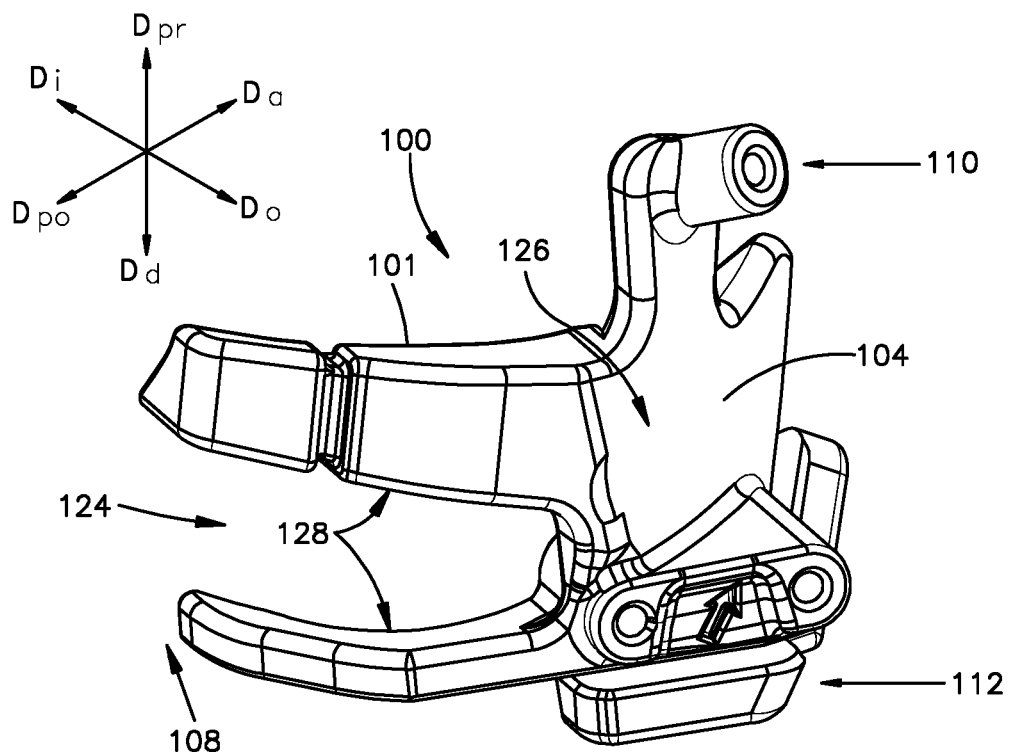
FIG. 1 shows an outer perspective view of an osteotomy guide according to one embodiment.
Figure 2:
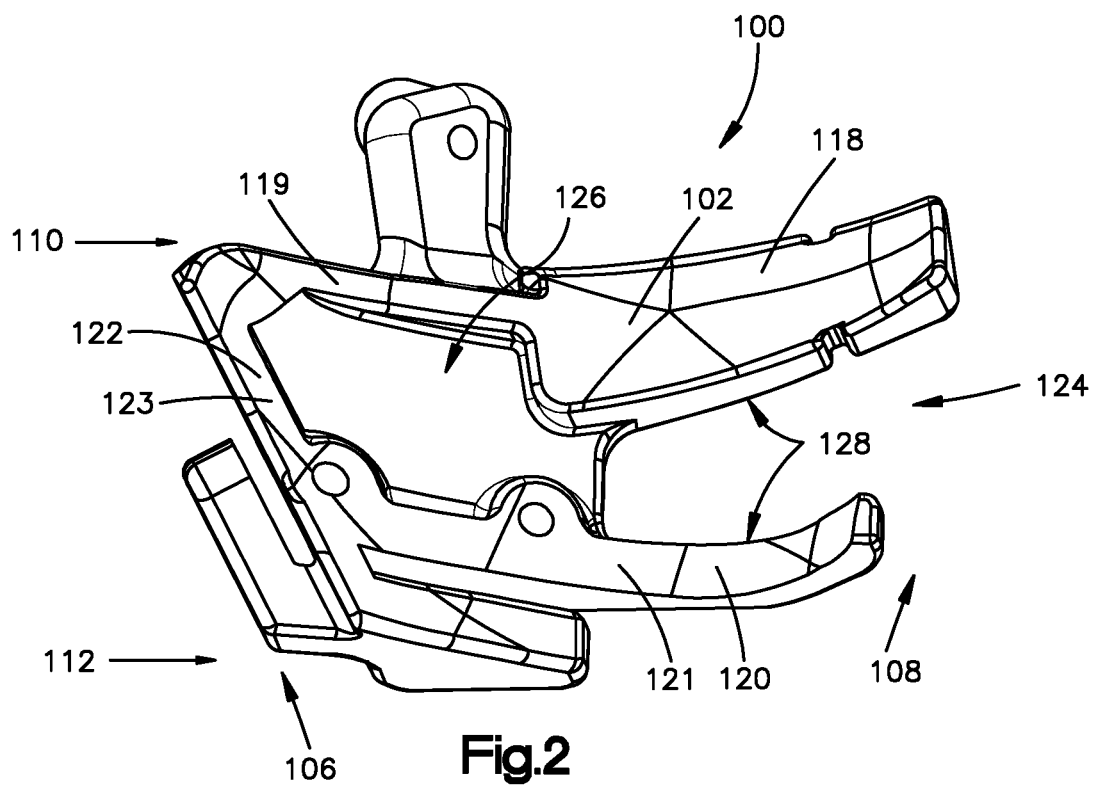
FIG. 2 shows an inner perspective view of the osteotomy guide of FIG. 1.

With general reference to FIGS. 1 to 8, an osteotomy guide 100 is shown according to one embodiment. The osteotomy guide 100 is configured to guide at least one cutting instrument to make a cut into a bone for an osteotomy procedure. The osteotomy guide 100 can be custom constructed to conform to a bone of a specific patient. In other words, the osteotomy guide 100 may be patient specific. The osteotomy guide 100 can be three-dimensionally (3-D) printed or can be fabricated in any other suitable manner. In at least some embodiments, the osteotomy guide 100 can include a one-piece body. The osteotomy guide 100 defines at least one ascending guide surface 134 and at least one transverse guide surface 138 (both labeled in FIGS. 5 and 6) that are configured to guide at least one cutting instrument, such as a saw blade, to make a cut into a bone such as a tibia, femur, fibula, humerus, ulna, radius, or other bone. The osteotomy guide 100 can be configured to guide a cut into the bone adjacent to a joint, the cut dividing the bone into first and second bone segments, the first bone segment being closer to the joint. The cut can then be enlarged by pivoting the first segment of the patient's bone relative to the second segment of the bone so as to realign the bone. For example, the cut can be enlarged to realign the weight bearing line, to balance the pressure in the knee, although other alignment procedures are contemplated. The enlarged cut can then be fixed by attaching a bone plate that extends across the cut from the first bone segment to the second bone segment so as to affix the bone on opposed sides of the enlarged cut. For illustrative purposes, the guide 100 will be described and shown relative to its use in making a cut in a tibia.

Referring more specifically to FIGS. 1 to 4, the osteotomy guide 100 has an inner surface 102, and an outer surface 104 opposite the inner surface 102 with respect to an outward direction $D_o$. In other words, the inner surface 102 is opposite from the outer surface 104 with respect to an inward direction $D_i$, where the inward direction $D_i$ is opposite the outward direction $D_o$. The inner surface 102 can be a bone facing surface configured to face the bone. Preferably, at least a portion of the inner surface 102 is configured to contact the bone, and thus, can be considered to be a bone contacting surface. The inner surface 102 can be contoured so as to conform to a surface of the bone. The contour can be generally concave or can be any suitable contour to match the surface of the bone. The outer surface 104 can be configured to face away from the bone. In some examples, the outer surface 104 can be substantially convex, although embodiments of the disclosure are not so limited.

The osteotomy guide 100 has an anterior end 106, and a posterior end 108 opposite the anterior end 106 with respect to a posterior direction $D_{po}$. In other words, the anterior end 106 is opposite the posterior end 108 with respect to an anterior direction $D_a$, where the anterior direction $D_a$ and posterior direction $D_{po}$ are opposite one another. Note that, as used herein, the anterior and posterior directions Da and $D_{po}$ together may also be referred to as a transverse direction. The osteotomy guide 100 can be configured to be positioned on the bone such that the anterior end 106 is adjacent an anterior side of the bone and the posterior end 108 is adjacent a posterior side of the bone. However, it will be understood that osteotomy guide 100 can be otherwise positioned. The anterior direction $D_a$ and the posterior direction $D_{po}$ can be perpendicular to both the inward and outward directions Din and $D_o$.

The osteotomy guide 100 has a proximal end 110, and a distal end 112 opposite the proximal end 110 with respect to a distal direction $D_d$. In other words, the proximal end 110 is opposite the distal end 112 with respect to a proximal direction $D_{pr}$, where the proximal direction $D_{pr}$ and distal direction $D_d$ are opposite one another. The osteotomy guide 100 is configured to be positioned on the bone such that the proximal end 110 is oriented towards a proximal end of the bone, and the posterior end 112 is oriented towards a distal end the bone. The proximal direction $D_{pr}$ and distal direction $D_d$ can be perpendicular to the inward direction Din, the outward direction $D_o$, the anterior direction $D_a$, and the posterior direction $D_{po}$.

The inner surface 102, and thus osteotomy guide 100, has at least two bone contacting regions that are configured to contact the bone when the osteotomy guide 100 is positioned along the bone. Each bone contacting region can be specifically sized and shaped to a contour of the bone of a particular patient. The at least two bone contacting regions can be arranged so as to define a gap 124 therebetween. The at least two bone contacting regions can include a first bone contacting region 118. The first bone contacting region 118 can be positioned closer to the proximal end 110 than a second bone contacting region 120 (discussed below). Thus, the first bone contacting region 118 may be considered to be a proximal bone contacting region. The first bone contacting region 118 can extend between the anterior end 106 and the posterior end 108. For example, the first bone contacting region 118 can be elongate as it extends between the anterior end 106 and the posterior end 108. In some embodiments, the first bone contacting region 118 can extend from the anterior end 106 to the posterior end 108. At least a portion, up to an entirety, of the first bone contacting region 118 can be contoured as it extends between the anterior end 106 to the posterior end 108 so as to conform to the bone. The contour can be generally concave or can be any suitable contour to match the surface of the bone. A posterior end, such as a free end, of the first bone contacting region 118 can be configured (e.g., sized and shaped) to hook a holding point of the bone when the osteotomy guide 100 is affixed to the bone. As used herein, the holding point can refer to a protrusion of the bone on a medial side of the bone.

Additionally, or alternatively, the at least two bone contacting regions can include a second bone contacting region 120. The second bone contacting region 120 can be offset from the first bone contacting region 118 along the distal direction $D_d$ so as to define a gap 124 therebetween. In other words, the first bone contacting region 118 can be offset from the second bone contacting region 120 along the proximal direction $D_{pr}$ so as to define a gap 124 therebetween. The second bone contacting region 120 can be positioned closer to the distal end 112 than the first bone contacting region 118. Thus, the second bone contacting region 122 may be considered to be a distal bone contacting region. The second bone contacting region 120 can extend between the anterior end 106 and the posterior end 108. For example, the second bone contacting region 120 can be elongate as it extends between the anterior end 106 and the posterior end 108. In some embodiments, the second bone contacting region 120 can extend from the anterior end 106 to the posterior end 108. At least a portion, up to an entirety, of the second bone contacting region 120 can be concave as it extends between the anterior end 106 to the posterior end 108 so as to conform to the bone. A posterior end, such as a free end, of the second bone contacting region 120 can be configured (e.g., sized and shaped) to hook the posterior ridge of the bone when the osteotomy guide 100 is affixed to the bone.

Additionally, or alternatively, the at least one bone facing surface can include a third bone contacting region 122. The third bone contacting region 122 can extend between the first bone contacting region 118 and the second bone contacting region 120. For example, the third bone contacting region 122 can extend from the first bone contacting region 118 to the second bone contacting region 120. The third bone contacting region 122 can be elongate as it extends between the first bone contacting region 118 and the second bone contacting region 120. The third bone contacting region 122 can be disposed at the anterior end 106 of the osteotomy guide 100. Thus, the third bone contacting region 122 can extend between the first bone contacting region 118 and the second bone contacting region 120 at the anterior end 106. Accordingly, the third bone contacting region 122 can be considered to be an anterior bone contacting region. The third bone contacting region 122 can be concave as it extends towards the posterior end 108. It will be understood that, in alternative embodiments, the osteotomy guide 100 can be implemented without the third bone contacting region 122 or the third bone facing surface can extend between the first bone contacting region 118 and the second bone contacting region 120 at a location that is offset from the anterior end 106.

The at least two bone contacting regions can provide a better fit on the bone than one larger bone contacting surface. For example, the gap 124 between the first bone contacting region 118 and the second bone contacting region 120 can provide space for bony protrusions to extend between the first bone contacting region 118 and the second bone contacting region 120.

The osteotomy guide 100 can include an anterior body portion 126, and a posterior body portion 128 that is offset from the anterior body portion 126 along the posterior direction $D_{po}$. The anterior body portion 126 can at least partially define the anterior end 106 and can extend from the anterior end 106 towards the posterior end 108. The posterior body portion 128 can at least partially define the posterior end 108 and can extend from the posterior end 108 towards the anterior end 106. The osteotomy guide 100 can include a proximal wall 119 that defines the first bone contacting region 118. The osteotomy guide 100 can include a distal wall 121 that defines the second bone contacting region 120. The distal wall 121 can be spaced from the proximal wall 119 along the distal direction Da so as to define the gap 124 therebetween. The anterior body portion 126, and hence the osteotomy guide 100, can include a third wall 123 that defines the third bone contacting region 122. The third wall 123 can extend between the proximal wall 119 and the distal wall 121, such as from the proximal wall 119 to the distal wall 121. The gap 124 can extend into the posterior end 108 towards the anterior end 106 such that the gap 124 is open at the posterior end 124. The gap 124 can extend towards and terminate at, for example, the third bone contacting region 122, such as at the third wall 123 that defines the third bone contacting region 122. It will be understood that, in some embodiments, the gap 124 can be closed at the posterior end 124.

The gap 124 extends into the inner surface 102 towards the outer surface 104. At least a portion of the gap 124 can extend through the outer surface 104. For example, the gap 124 can extend through the outer surface 104 at the posterior body portion 128. In other words, at least a portion, such as an anterior portion, of the gap 124 can be open at the inner surface 102 and the outer surface 104. At least a portion of the gap 124 can terminate at the outer surface 104. For example, the gap 124 can terminate at the outer surface 104 at the anterior body portion 126. Thus, at least a portion, such as an anterior portion, of the gap 124 can be open at the inner surface 102 and closed at the outer surface 104. It will be understood that, in some embodiments, the anterior portion of the gap 124 can be open at the outer surface 104. Additionally, or alternatively, in some embodiments, the posterior portion of the gap 124 can be closed at the outer surface 104. In some embodiments, the gap 124 can have a dimension along the proximal direction $D_{pr}$ or distal direction $D_d$ that is greater than, or equal to, a dimension of at least one, such as both, of the first bone contacting region 118 and the second bone contacting region 118 along the same direction.

Referring to FIGS. 5 to 8, in embodiments where the gap 124 extends through the inner surface 102 and the outer surface 104, the posterior body portion 128, and thus osteotomy guide 100, can include a proximal arm 130, and a distal arm 132 that is offset from the proximal arm 130 with respect to the distal direction $D_d$. The proximal arm 130 and the distal arm 132 can be separated from one another by the gap 124. The proximal arm 130 can extend from the anterior body portion 126 towards the posterior end 108. Thus, the proximal arm 130 can have a first end that is attached to the anterior body portion 126 and a second end that is spaced from the first end along the posterior direction $D_{po}$. The second end can be a free end of the proximal arm 130. Similarly, the distal arm 132 can extend from the anterior body portion 126 towards the posterior end 108. Thus, the distal arm 132 can have a first end that is attached to the anterior body portion 126 and a second end that is spaced from the first end along the posterior direction $D_{po}$. The second end can be a free end of the distal arm 132. In some embodiments, the proximal arm 130 can be angled away from the distal arm 132 as the proximal arm 130 extends towards the posterior end 108. It will be understood that the precise shape of each of the first and second arm may vary based on the specific curvatures of the patient's bone.

Figure 3:
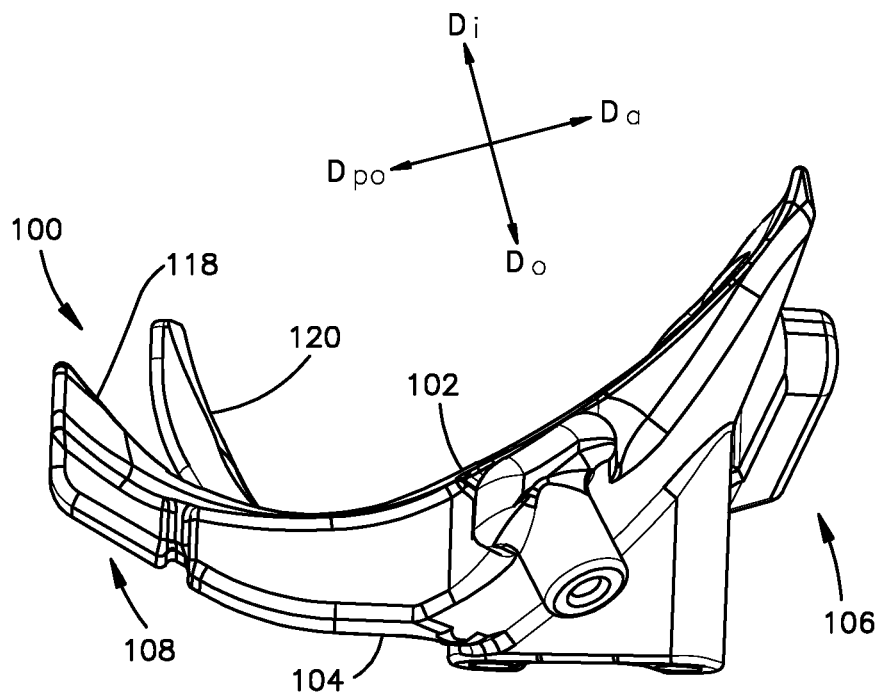
FIG. 3 shows plan view of a proximal end of the osteotomy guide of FIG. 1.
Figure 4:
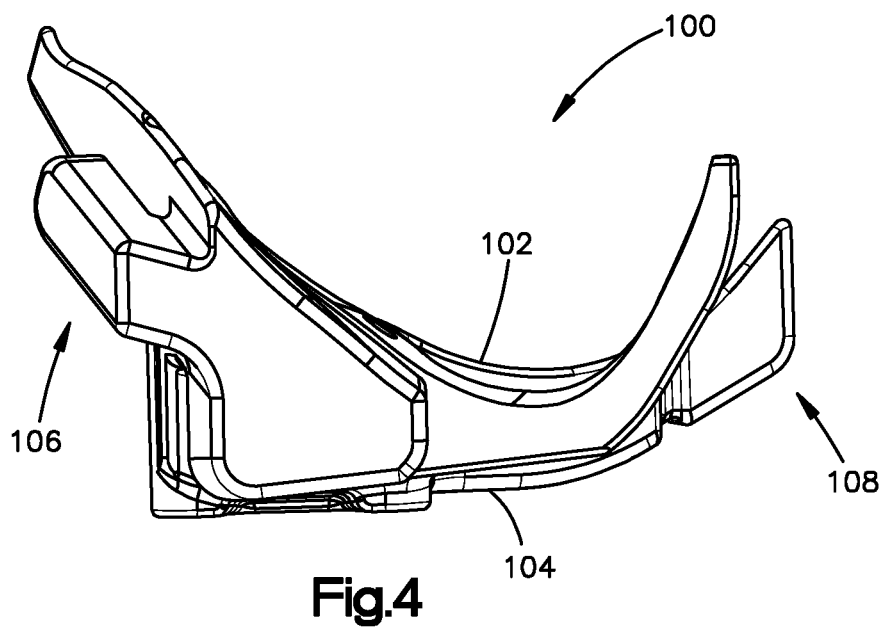
FIG. 4 shows plan view of a distal end of the osteotomy guide of FIG. 1.
Figure 7:
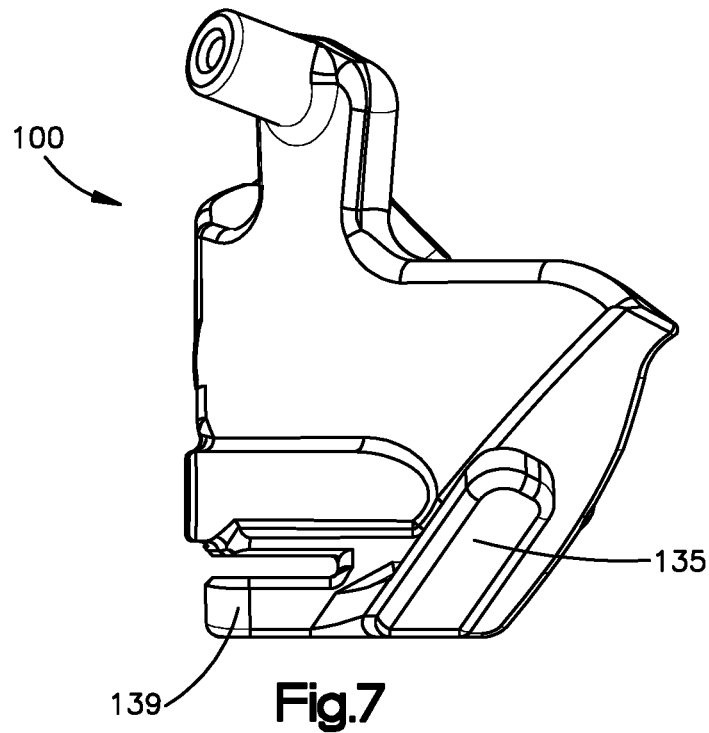
FIG. 7 shows elevation view of an anterior end of the osteotomy guide of FIG. 1.
Figure 8:
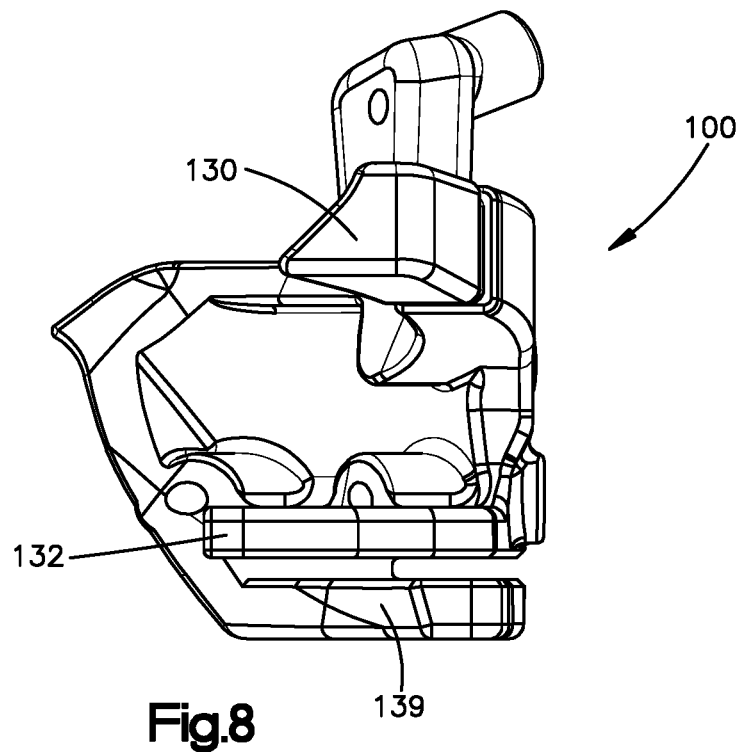
FIG. 8 shows elevation view of a posterior end of the osteotomy guide of FIG. 1.
Figure 10:
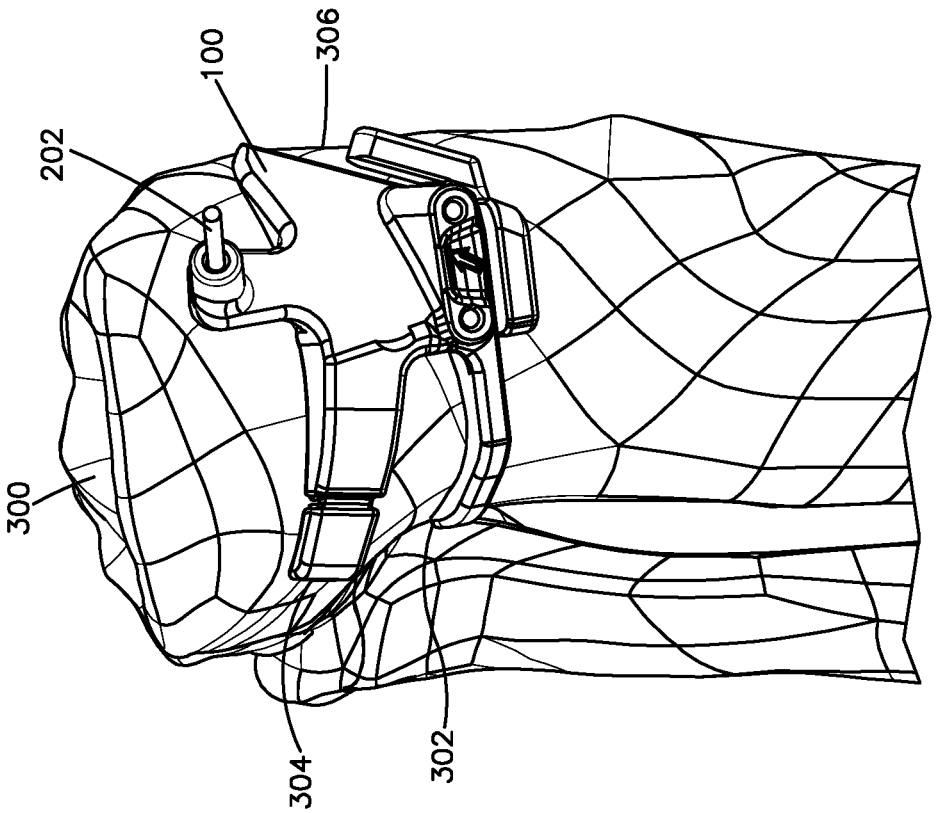
FIG. 10 shows a perspective view of a tibia and fibula with the osteotomy guide of FIG. 1 attached to the tibia.
Figure 9:
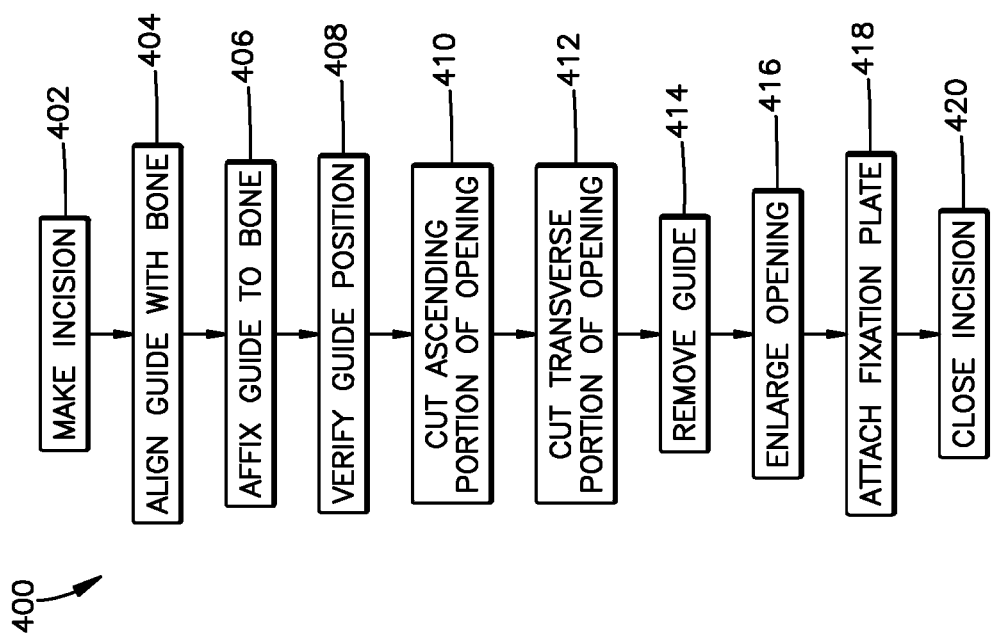
FIG. 9 shows a simplified block diagram of a surgical method according to one embodiment.
Figure 12:
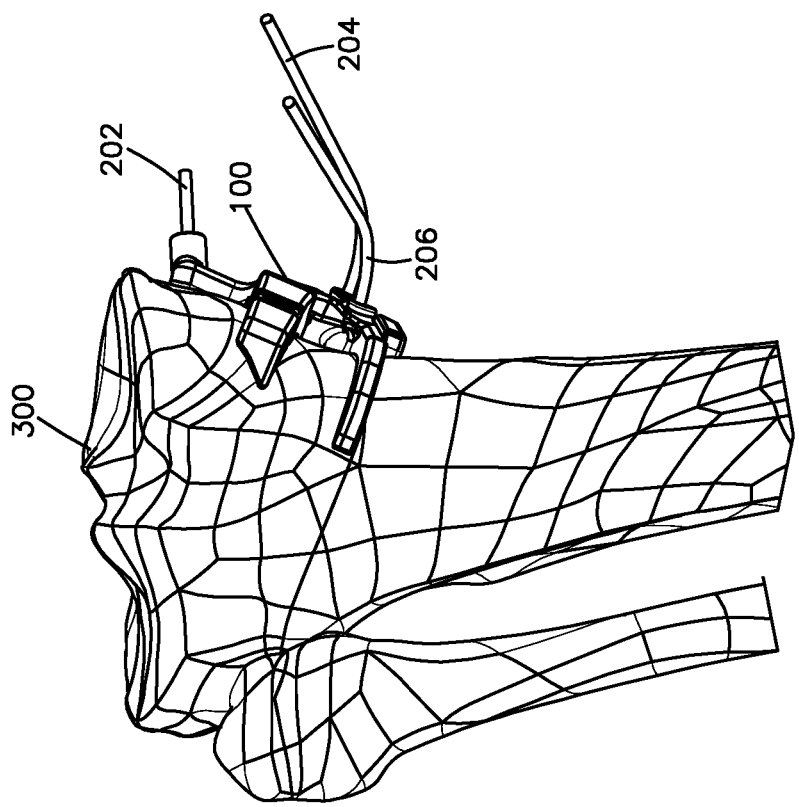
FIG. 12 shows a perspective view of the tibia, fibula, and osteotomy guide of FIG. 10 along the anterior direction.

The proximal arm 130 can include at least a portion, such as a posterior portion, of the first bone contacting region 118. The distal arm 132 can include at least a portion, such as a posterior portion, of the second bone contacting region 120. The first bone contacting region 118 has a first curvature, and the second bone contacting region 120 has a second curvature that is different from the first curvature. For example, the second curvature can be greater than the first curvature. Thus, the second bone contacting region 120 can curve further inward than the first bone contacting region 118 as can be seen in FIG. 3. It will be understood that, in alternative embodiments, the first and second curvatures may be different from that shown and may vary based on the curvatures of a particular patient's bone.

With continued reference to FIGS. 5 and 6, the osteotomy guide 100 can have at least one ascending guide surface that is configured to guide the cutting instrument to make an ascending cut into the bone. However, it will be understood that, in alternative embodiments, the guide 100 can be devoid of an ascending guide surface. The ascending cut may be made, for example, around the tibial tuberosity behind the patellar tendon. Thus, the osteotomy guide 100 can be configured (e.g., sized and shaped) such that each of the at least one ascending guide surface is aligned with the tibial tuberosity when the osteotomy guide 100 is affixed to the bone. Each of the at least one ascending guide surface can be disposed at the anterior end 106 of the osteotomy guide 100.

The at least one ascending guide surface can include a first ascending guide surface 134. The first ascending guide surface 134 can extend along an ascending axis AA that extends along an ascending direction so as to at least partially define a transverse cutting path into the bone. The ascending direction is angularly offset with respect to the proximal direction $D_{pr}$ and the transverse direction. For example, the ascending direction can extend at an angle that is between the proximal direction $D_{pr}$ and the transverse direction. Thus, the first ascending guide surface 134 can be angled towards the anterior direction $D_a$ as the first ascending guide surface 134 extends towards the proximal end 110. The third wall 123 can define the first ascending guide surface 134.

In some embodiments, the at least one ascending guide surface can include a second ascending guide surface 136 that is offset from the first ascending guide surface 134 so as to define an ascending groove 114 therebetween. The second ascending guide surface 136 can extend along the ascending axis AA that extends along the ascending direction so as to at least partially define an ascending cutting path into the bone. Thus, the second ascending guide surface 136 can be angled towards the anterior direction Da as the second ascending guide surface 134 extends towards the proximal end 110. At least a portion of the first ascending guide surface 134 can face the second ascending guide surface 136 so as to define the ascending groove 114 therebetween. The ascending groove 114 can be configured to guide a cutting instrument to make an ascending cut into the bone. In some embodiments, the second ascending guide surface 136 can be substantially parallel to the first ascending guide surface 134. The first ascending guide surface 134 can have a length along the ascending direction that is greater than that of the second ascending guide surface 136, although embodiments of the disclosure are not so limited.

In embodiments having the second ascending guide surface 136, the osteotomy guide 100 can include an ascending leg 135 that defines the second ascending guide surface 136. The ascending leg 135 can have a first end that is attached to the anterior body portion 126, and a second end that is offset from the first end along the ascending direction. The ascending leg 135 can be integral and monolithic with the anterior body portion 126, although embodiments of the disclosure are not so limited. The second end can be a free end that is free from attachment to the anterior body portion 126 or any other portion of osteotomy guide 100. The ascending groove 114 can extend into osteotomy guide 100 along a descending direction opposite the ascending direction. As such, a proximal end of the ascending groove 114 can be open, and a distal end of the ascending groove 116 can be closed, where the distal end is offset from the proximal end along the descending direction. It will be understood that, in alternative embodiments, the ascending groove 114 can terminate adjacent to the first end or can be open at both the first and second ends.

The osteotomy guide 100 can have at least one transverse guide surface that is configured to guide a cutting instrument to make a transverse cut into the bone. Each transverse guide surface can be disposed at the distal end 112 of the osteotomy guide 100. Each transverse guide surface can be offset from the gap 124 with respect to the distal direction $D_o$. For example, each transverse guide surface can be offset from the second bone contacting region 120 with respect to the distal direction $D_o$.

The at least one transverse guide surface can include a first transverse guide surface 138. The first transverse guide surface 138 can extend along a transverse axis $A_T$ that extends along the anterior direction $D_a$ and the posterior direction $D_{po}$ (herein, collectively referred to as the transverse direction) so as to at least partially define a transverse cutting path into the bone. The ascending axis AA and transverse axis $A_T$ can intersect one another.

In some embodiments, the at least one transverse guide surface can include a second transverse guide surface 140 that is offset from the first transverse guide surface 138 so as to define a transverse groove 116 therebetween. The second transverse guide surface 140 can extend along the transverse axis $A_T$ that extends along the transverse direction so as to at least partially define the transverse cutting path into the bone. At least a portion of the first transverse guide surface 138 can face the second transverse guide surface 140 so as to define the transverse groove 116 therebetween. The transverse groove 116 can be configured to guide a cutting instrument to make a transverse cut into the bone. The cutting instrument may be the same as, or different from, the cutting instrument used to make the ascending cut. In some embodiments, the second transverse guide surface 140 can be substantially parallel to the first transverse guide surface 138. The first transverse guide surface 138 can have a length along the posterior direction $D_{po}$ that is greater than that of the second transverse guide surface 140, although embodiments of the disclosure are not so limited.

In embodiments having the second transverse guide surface 140, the osteotomy guide 100 can include a transverse leg 139 that defines the second transverse guide surface 140. The transverse leg 139 can have a first end that is attached to the anterior body portion 126 at a bridge 137, and a second end that is offset from the first end along the posterior direction $D_{op}$. The transverse leg 139 can be integral and monolithic with the anterior body portion 126, although embodiments of the disclosure are not so limited. The second end can be a free end that is free from attachment to the anterior body portion 126 or any other portion of the osteotomy guide 100. The transverse groove 116 can extend into the osteotomy guide 100 along the anterior direction. As such, a posterior end of the transverse groove 116 can be open, and an anterior end of the transverse groove 116 can be closed, where the posterior end is offset from the anterior end along the posterior direction $D_{po}$. It will be understood that, in alternative embodiments, the transverse groove 116 can terminate adjacent to the first end or can be open at both the first and second ends.

As can be seen in FIGS. 5 and 6, the bridge 137 separates the ascending groove 114 from the transverse groove 116. As such, when the ascending cut and transverse cut are made in the bone, the bridge 137 can obstruct the cutting of the segment of the bone that joins the ascending cut and transverse cut and that underlies the bridge 137. In this example, the bridge 137 obstructs the transverse cut. Thus, the first transverse guide surface 138, and consequently the transverse cutting groove 116, terminates such that it does not intersect the ascending cutting groove 114. As such, the transverse cut may need to be extended after the osteotomy guide 100 is removed so as to join the transverse cut to the ascending cut.

The osteotomy guide 100 can define at least one fixation hole that extends through the osteotomy guide 100. Each fixation hole can be configured to receive a fixation pin, such as a Kirschner wire, therethrough so as to affix the osteotomy guide 100 to the bone. Each fixation hole can extend through the inner surface 102 and the outer surface 104 of the osteotomy guide 100. It will be understood that the locations of the fixation holes can vary from the embodiment shown.

In one example, the at least one fixation hole can include a proximal fixation hole 142 that is offset from the first bone contacting region 118 with respect to the proximal direction $D_{pr}$. The osteotomy guide 100 can include a neck 144 that extends from the anterior body portion 126 along the proximal direction $D_{pr}$. The proximal fixation hole 142 can extend through the neck 144. The neck 144 can have an inner surface 145 that is configured to face the bone. The inner surface 145 of the neck 144 can be offset with respect to the proximal bone facing surface with respect to the outward direction $D_o$. Consequently, when the proximal bone facing surface is aligned with the bone, the inner surface 145 of the neck 144 can be spaced from the bone so as to accommodate soft tissue between the inner surface 145 and the bone. Further, the proximal fixation hole 142 can correspond to a location of a hole of the bone fixation plate that is to be affixed to the bone. Thus, proximal fixation hole 142 can act as a guide for forming a hole in the bone that is used for both (i) a fixation pin that secures the osteotomy guide 100 to the bone and (ii) a bone anchor that affixes the bone fixation plate to the bone after the cut in the bone has been enlarged.

The at least one fixation hole can include at least one, such as two, distal bone fixation holes 146 and 148. Each distal bone fixation hole 146 and 148 can be offset from the proximal bone fixation hole 142 with respect to the distal direction $D_d$. Each distal bone fixation hole 146 and 148 can extend through the anterior body portion 126 of the osteotomy guide 100. In embodiments having first and second distal bone fixation holes 146 and 148, the first distal bone fixation hole 146 can be spaced from the second distal bone fixation hole 148 along the anterior direction $D_a$. The first and second distal bone fixation holes 146 and 148 can be aligned along a direction that is substantially parallel with the at least one transverse guide surface 138.

The osteotomy guide 100 can be a unitary body having the anterior body portion 126, the proximal arm 130, the distal arm 132, the ascending leg 135, and the transverse leg 139. For example, the anterior body portion 126, the proximal arm 130, the distal arm 132, the ascending leg 135, and the transverse leg 139 can be integral and monolithic with one another. In one such example, the osteotomy guide 100 can be 3-D printed as a single monolithic body. Forming the osteotomy guide 100 as a single monolithic body can limit costs of 3-D printing the osteotomy guide 100 and can simplify the manufacturing process. In alternative embodiments, various components of the osteotomy guide 100 can be affixed, such as glued, welded, fastened, or otherwise coupled to, the anterior body portion 126. Providing the osteotomy guide 100 as a unitary body can simplify handling of the osteotomy guide 100 and improve cutting accuracy over conventional guides that include two or more movable parts where stability of the movable parts can be difficult to maintain.

In one embodiment, a method of fabricating the osteotomy guide 100 can include obtaining a 3-D computer model of the patient's anatomy. This obtaining step can comprise receiving the 3-D computer model in a computer. Additionally, or alternatively, this obtaining step can comprise obtaining at least one image, such as a plurality of images, of the patient's anatomy using an imaging machine, such as a CT or MRI scan, and generating the 3-D computer model of the patient's anatomy from the image. The method can comprise a step of generating a 3-D computer model of the osteotomy guide 100 that conforms to the patient's anatomy. The method can comprise a step of 3-D printing the osteotomy guide 100 based on the 3-D computer model of the osteotomy guide 100.

Figure 11:
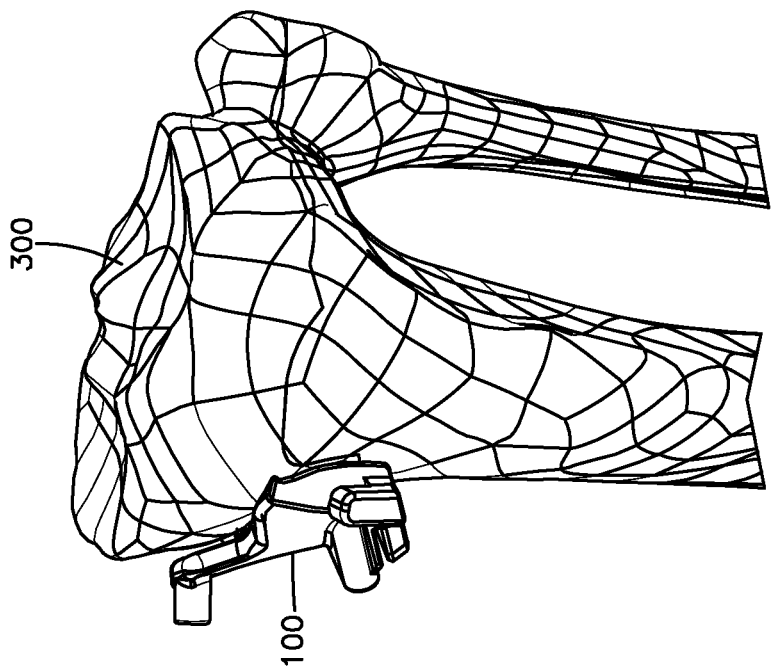
FIG. 11 shows a perspective view of the tibia, fibula, and osteotomy guide of FIG. 10 along the posterior direction.

Turning now to FIGS. 9 to 14, a surgical method 300 will now be described. It will be understood that various steps of the surgical method can be performed by different healthcare professionals. Accordingly, the surgical method can be divided into various sub-methods that can be performed separately of one another. The method can comprise an incision step 402 that comprises making an incision in the patient to access the patient's bone 300. The method can comprise an alignment step 404 that comprises aligning the osteotomy guide 100 onto the bone 300. For example, the alignment step 404 can comprise covering the posterior end (e.g., free end) of the first bone contacting region 118 around a holding point 304 of the bone 300. The alignment step 404 can comprise hooking the posterior end (e.g., free end) of the second bone contacting region 120 around the posterior ridge 302 of the bone 300. The alignment step 404 can comprise aligning the at least one ascending guide surface 134 and/or groove 114 with the tibial tuberosity 306. When the first bone facing surface is aligned with the bone 300, the inner surface 145 of the neck 144 can be spaced from the bone 300 as shown in FIG. 11 so as to accommodate soft tissue between the inner surface 145 and the bone 300.

With the osteotomy guide 100 aligned, the osteotomy guide 100 can be affixed to the bone 300 in step 406. The affixation step 406 can comprises inserting a fixation pin, such as a Kirschner wire, through at least one fixation hole in the osteotomy guide and into the bone. For example, the fixation step 406 can comprise inserting a fixation pin 202 through at least one proximal fixation hole 142 and into the bone 300. The fixation step 406 can comprise inserting a fixation pin through at least one distal fixation hole and into the bone 300. For example, the fixation step 406 can comprise inserting a fixation pin 204 through the first distal fixation hole 146 and into the bone 300. The fixation step 406 can comprise inserting a fixation pin 206 through a second distal fixation hole 148 and into the bone 300.

The method 400 can comprise a step 408 of verifying that the osteotomy guide 100 is positioned correctly. The verifying step 408 can comprise using x-ray for fluoroscopy to verify the position of the osteotomy guide 100. The method 400 comprises making the ascending portion 308 (labeled in FIG. 15) of the cut 307 into the bone (step 410) as shown in FIG. 13, and making the transverse portion 310 (labeled in FIG. 15) of the cut 307 into the bone 300 (step 412) as shown in FIG. 14. Step 410 can be performed before or after step 412. The ascending cut 308 and the transverse cut 310 can be each made with a cutting instrument such as a saw blade 208, and can be made with the same cutting instrument or with different cutting instruments. In one embodiment, the saw blade 208 can have a proximal end (not shown) that attaches to the saw, and a distal end 210 that is offset from the saw along an insertion direction Din. The saw blade 208 can be elongate from its proximal end to its distal end 210, and can have a cutting edge at its distal end 210. The saw can oscillate the blade 208 along a direction that is perpendicular to the insertion direction Din, and can cut into the bone 300 along the insertion direction Din. The depth of the saw blade 208 can be controlled using depth markings on the saw blade 208, using a stop attached to the saw blade 208, or using any other suitable technique. To accommodate the cutting instrument, the at least one distal fixation pin 204 and 206 can be bent out of the path of the cutting instrument as shown in FIGS. 13 and 14. The bend of the fixation pins 204 and 206 can further secure the osteotomy guide 100 to the bone 300.

Figure 15:
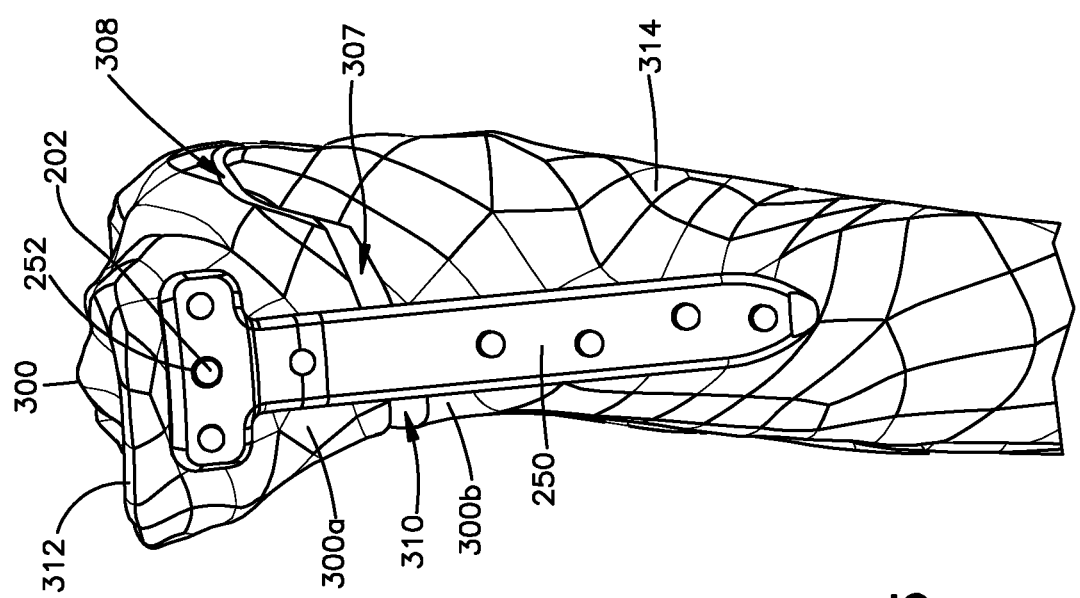
FIG. 15 shows an anterior view of the tibia and fibula of FIG. 10 after a cut has been formed in the tibia and a fixation plate has been attached to the tibia.
Figure 16:
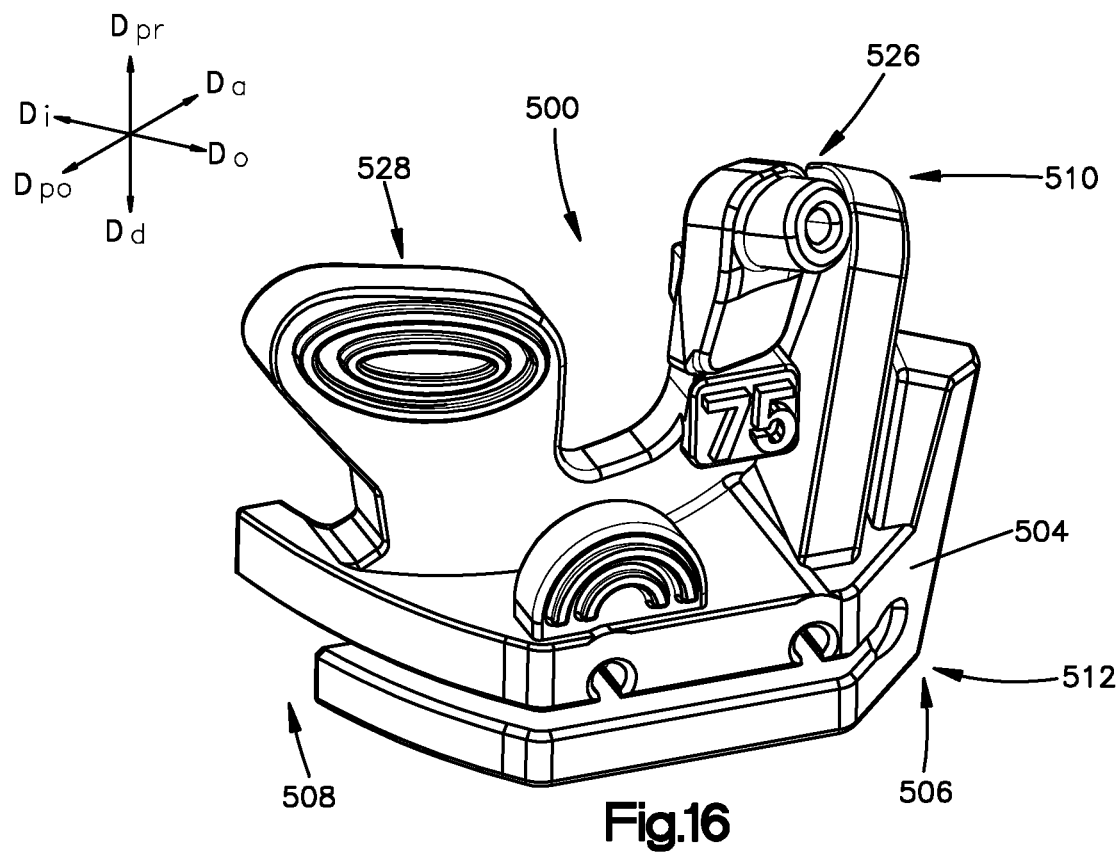
FIG. 16 shows an outer perspective view of an osteotomy guide according to another embodiment.
Figure 17:
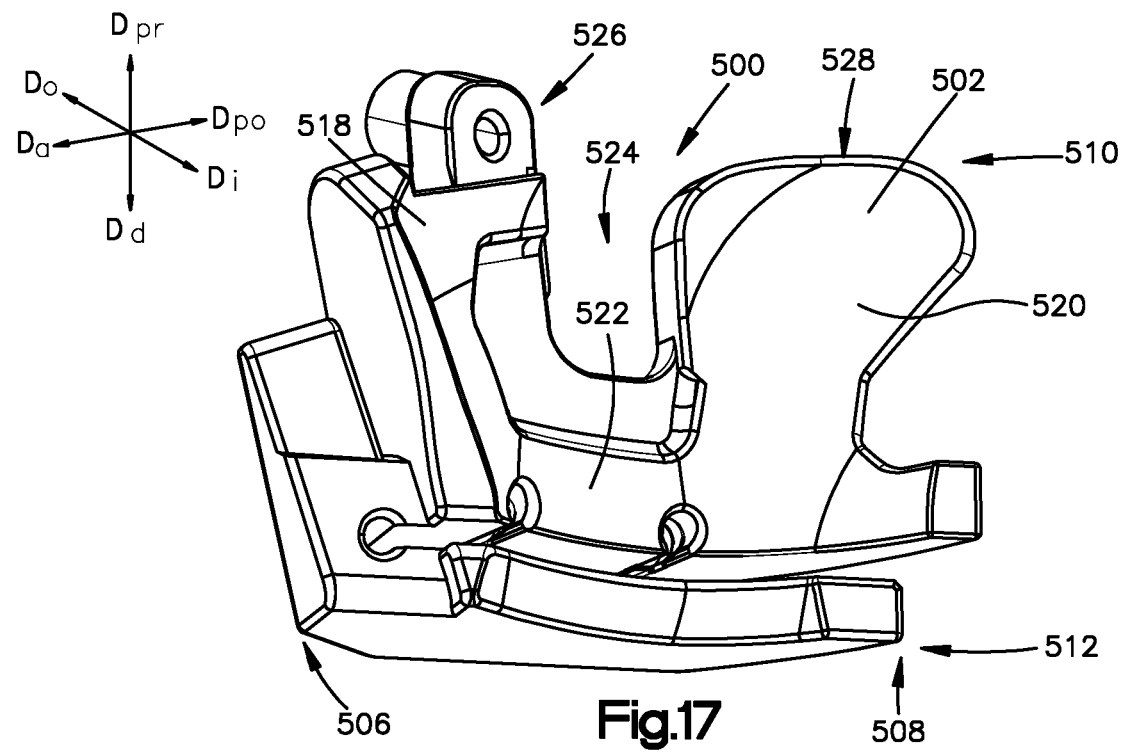
FIG. 17 shows an inner perspective view of the osteotomy guide of FIG. 16.
Figure 18:
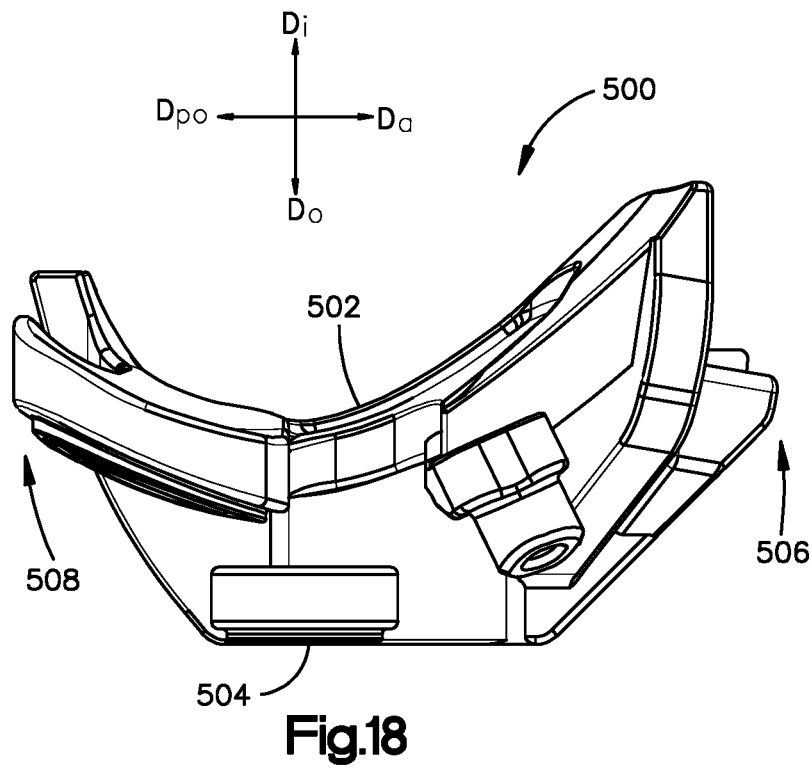
FIG. 18 shows plan view of a proximal end of the osteotomy guide of FIG. 16.
Figure 19:
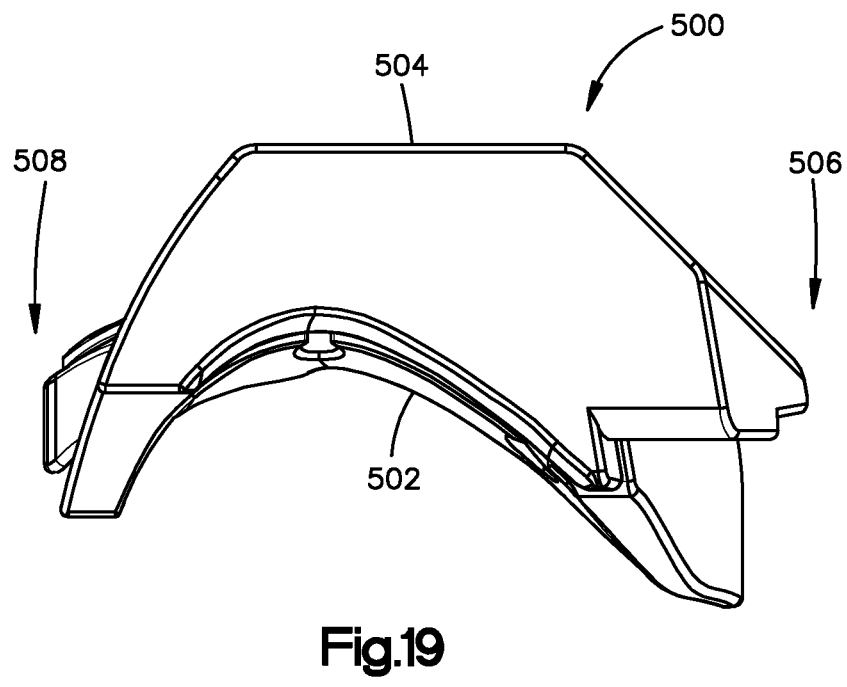
FIG. 19 shows plan view of a distal end of the osteotomy guide of FIG. 16.
Figure 22:
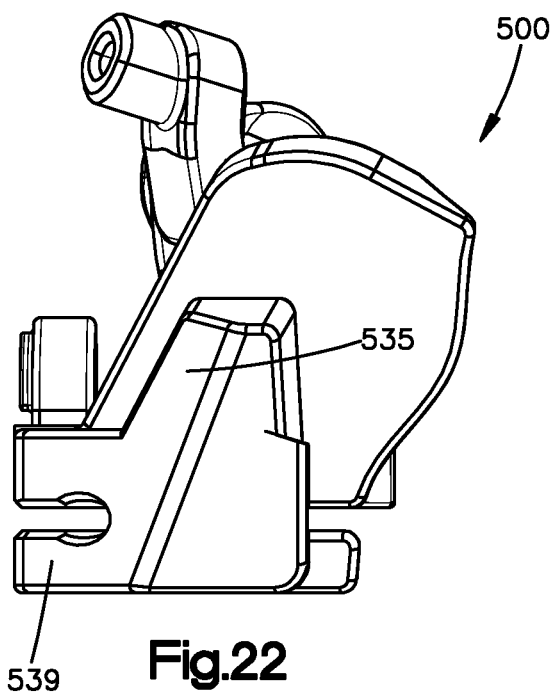
FIG. 22 shows elevation view of an anterior end of the osteotomy guide of FIG. 16.
Figure 23:
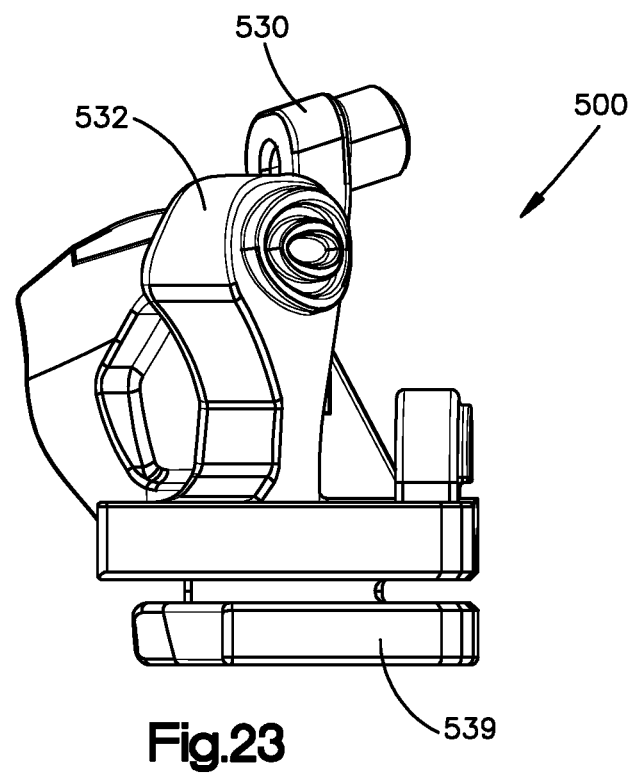
FIG. 23 shows elevation view of a posterior end of the osteotomy guide of FIG. 16.
Figure 24:
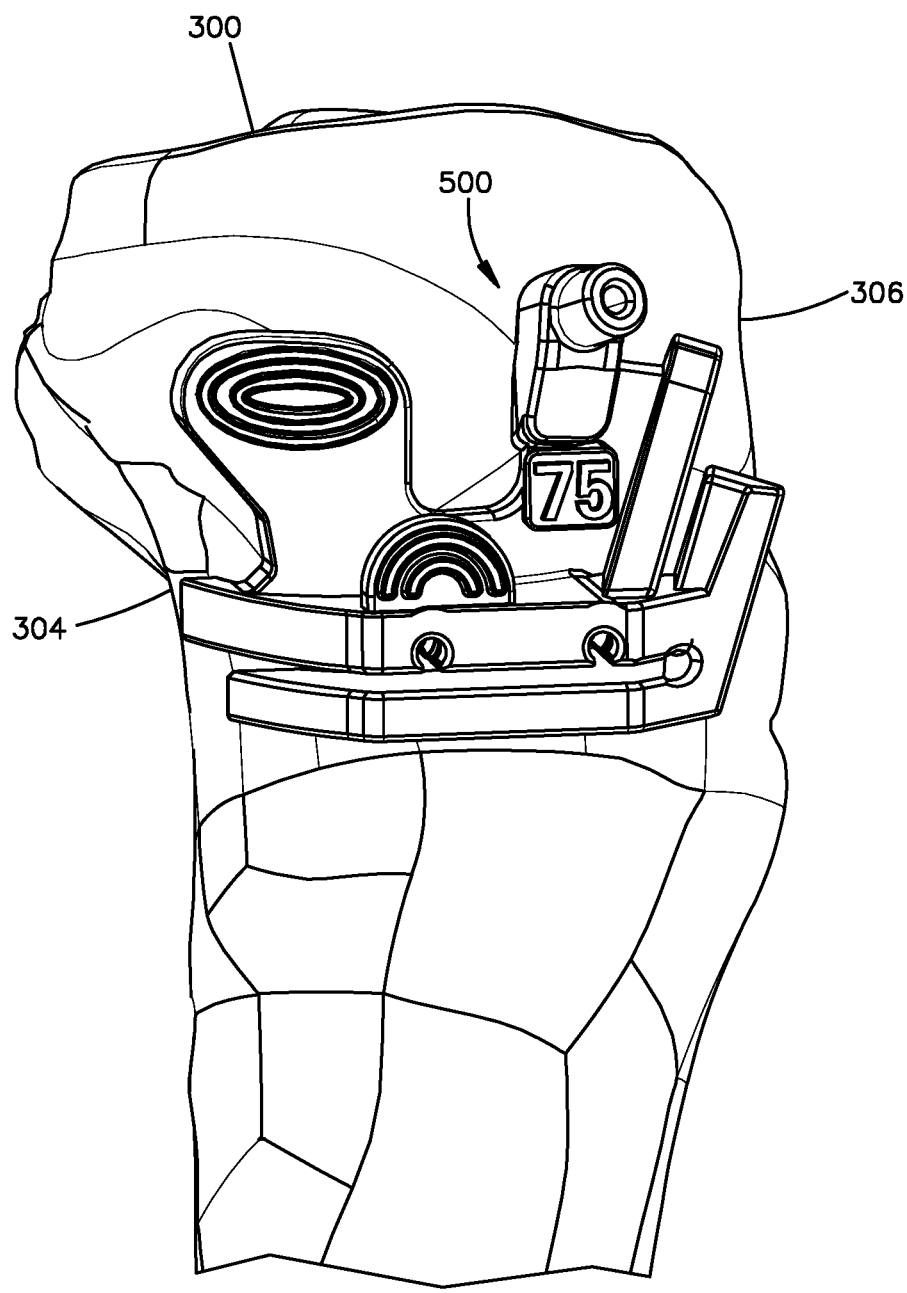
FIG. 24 shows a perspective view of a tibia along with the osteotomy guide of FIG. 16 attached to the tibia.
Figure 27:
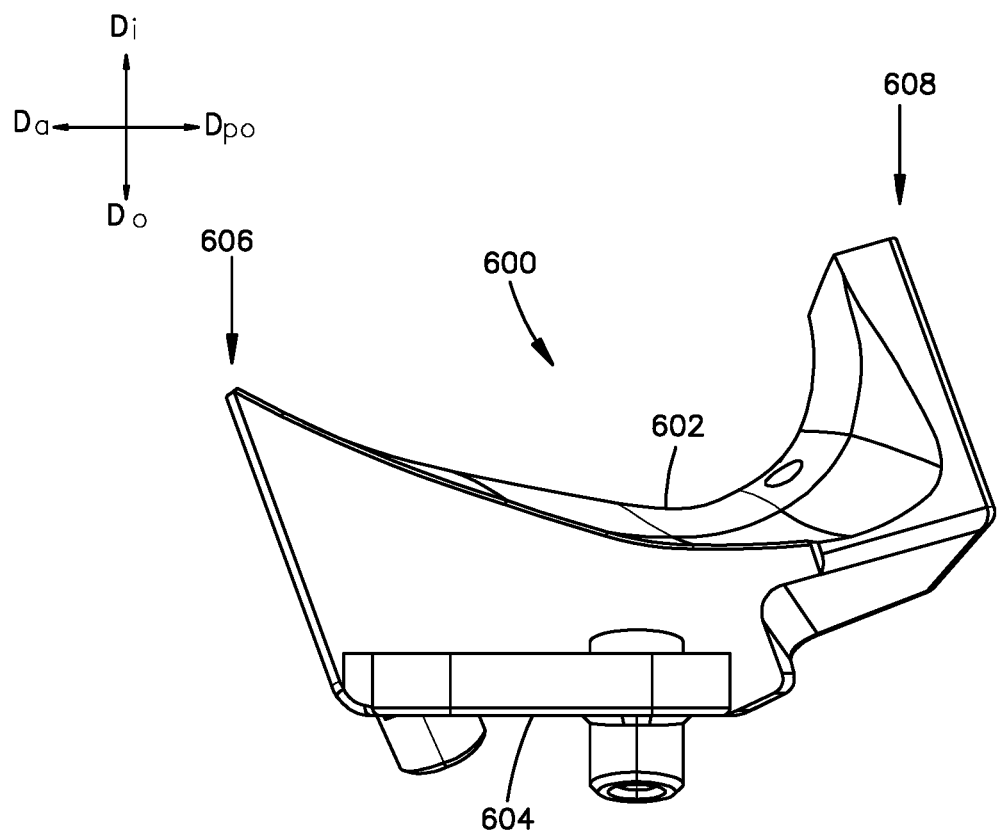
FIG. 27 shows plan view of a proximal end of the osteotomy guide of FIG. 25.
Figure 28:
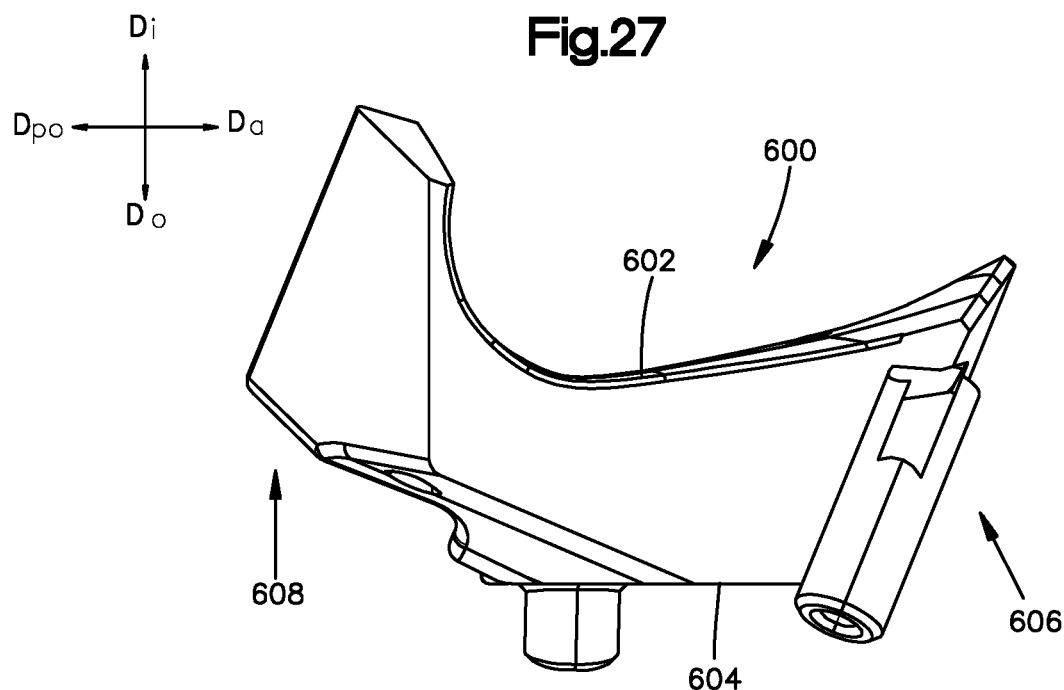
FIG. 28 shows plan view of a distal end of the osteotomy guide of FIG. 25.
Figure 32:
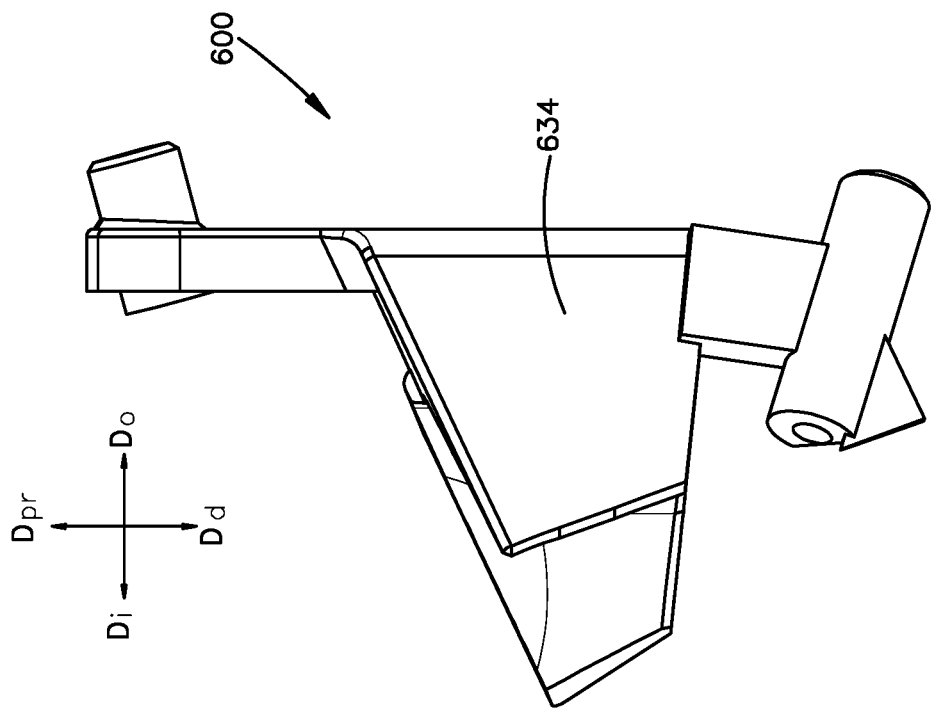
FIG. 32 shows elevation view of an anterior end of the osteotomy guide of FIG. 25.
Figure 31:
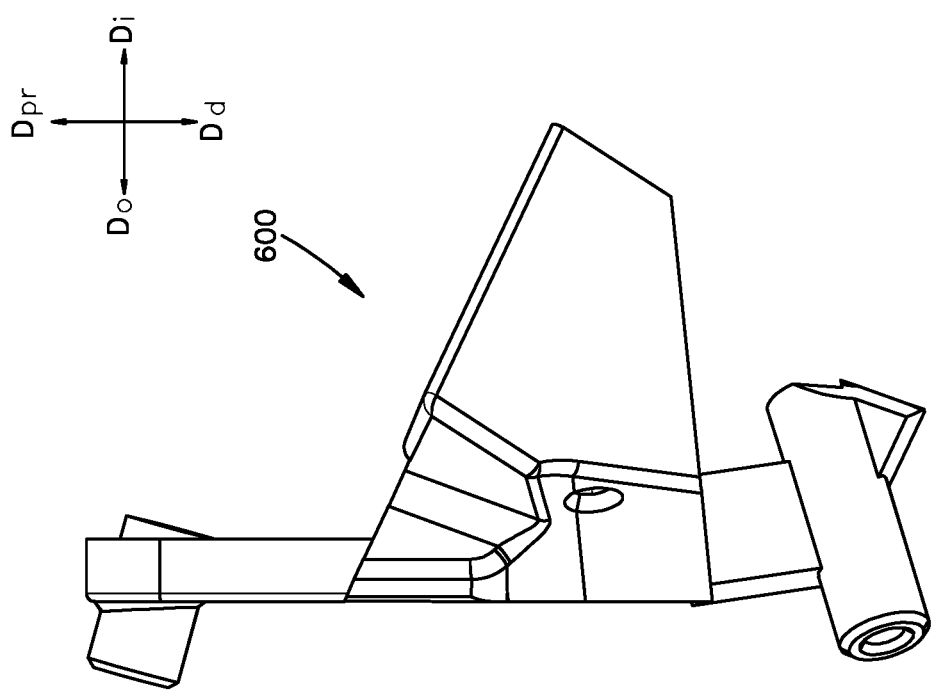
FIG. 31 shows elevation view of a posterior end of the osteotomy guide of FIG. 25.
Figure 34:
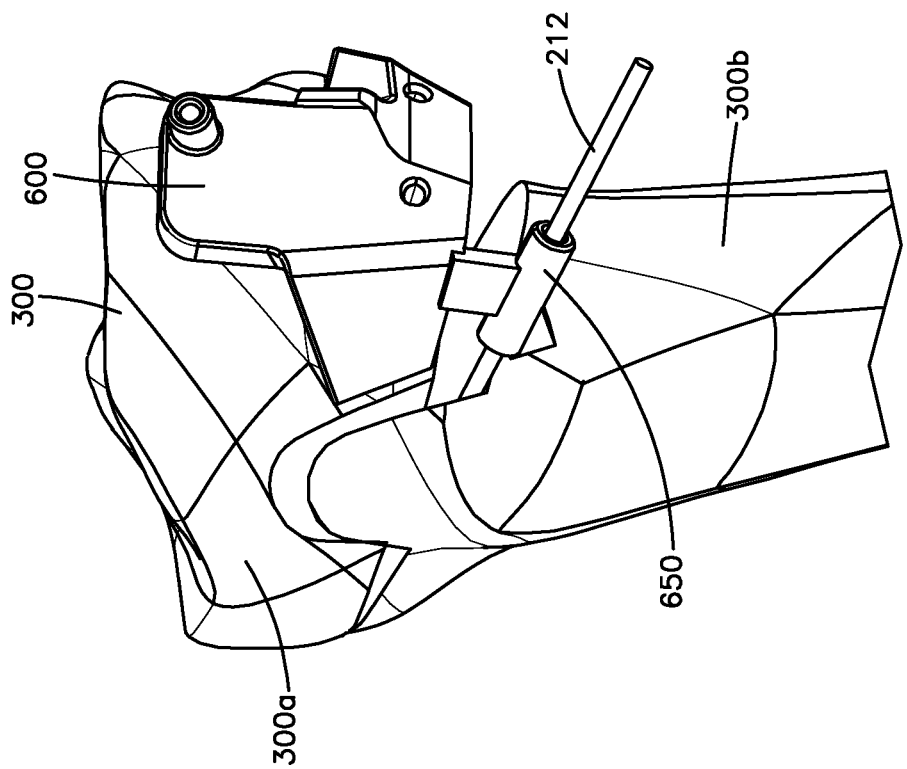
FIG. 34 shows a perspective view of the tibia and guide of FIG. 33 with an osteotomy cut in the tibia enlarged.
Figure 33:
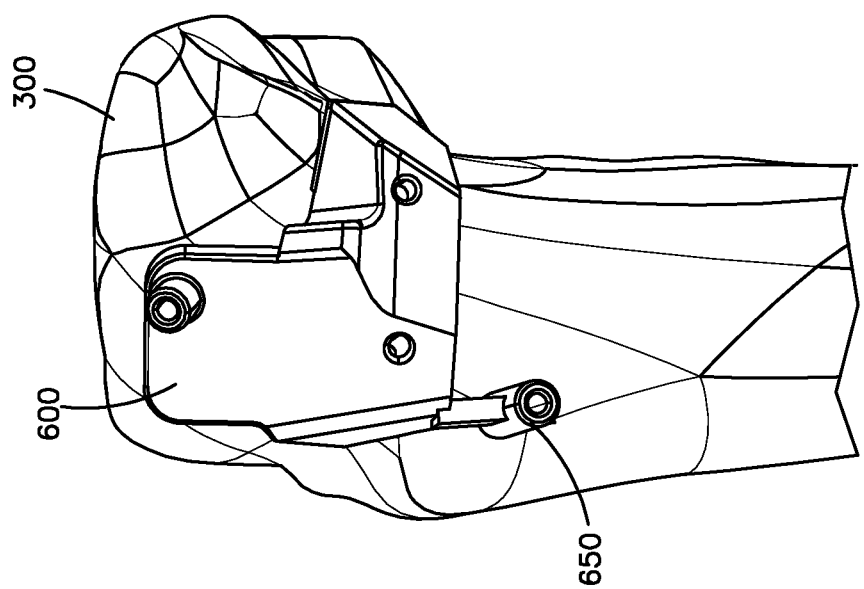
FIG. 33 shows a perspective view of a tibia along with the osteotomy guide of FIG. 25 attached to a tibia.

With specific reference to FIGS. 11 and 15, the method can comprise, after cutting the bone 300, a step 414 of removing the osteotomy guide 100. Step 414 can comprise removing the at least one distal fixation pin 204 and 206 before or after removing the osteotomy guide 100. The proximal fixation pin 202 can optionally be left in place. After removing the osteotomy guide 100, the method can comprise enlarging the cut 307 in the bone so as to realign bone. For example, the cut can be enlarged to realign the weight bearing line, to balance the pressure in the knee, although other alignment procedures are contemplated. The enlarging step 416 can comprise using a cutting instrument, such as a chisel or saw, to further enlarge the cut 307 so as to enable a proximal portion 312 of the bone 300 to pivot relative to a distal portion of the bone 314, where the proximal and distal portions 312 and 314 of the bone 300 are separated by the cut 307. For example, when cutting the ascending portion 308 and the transverse portion 310 of the cut 307, the cut might not be made through the portion of the bone that underlies the bridge 137 of the osteotomy guide 100. Therefore, after the osteotomy guide 100 is removed, a cutting instrument can be used to extend the transverse portion 310 of the cut 307 to the ascending portion 308 of the cut 307. Once cutting is complete, the cut divides the bone into first and second bone segments 300a and 300b, the first bone segment 300a being closer to the joint than the second bone segment 300b. The enlarging step 414 can comprise enlarging the opening formed by the cut 307 by moving, such as rotating or translating, the first bone segment 300a away to the second bone segment 300b. Enlarging the cut 307 can comprise inserting wedges (discussed below) or other instruments, such as a distractor instrument, into the cut 307 so as to achieve a desired correction angle of the articular surface of the joint.

After enlarging the cut 307, a bone fixation plate 250 can be affixed to the proximal portion 312 and the distal portion 314 of the bone 300 in step 418 so as to maintain the cut 307 in the enlarged position. In one embodiment, step 418 can comprise aligning the bone fixation plate 250 with the bone 300 by receiving a fixation hole 252 of the bone fixation plate 250 over the proximal fixation pin 202 (if the fixation pin 202 were left in place as described above). The bone fixation plate 250 can be affixed to the bone 300 by inserting bone anchors through the bone fixation plate 250 and into the proximal portion 312 and distal portion 314 of the bone 300. In step 420, the incision can be closed.

Turning now to FIGS. 16 to 24, an osteotomy guide 500 is shown according to another embodiment. The osteotomy guide 500 is configured to guide at least one cutting instrument to make a cut into a bone for an osteotomy procedure. The osteotomy guide 500 can be custom constructed to conform to a bone of a specific patient. In other words, the osteotomy guide 500 may be patient specific. The osteotomy guide 500 can be three-dimensionally (3-D) printed or can be fabricated in any other suitable manner. In at least some embodiments, the osteotomy guide 500 can include a one-piece body. The osteotomy guide 500 defines at least one ascending guide surface 534 and at least one transverse guide surface 538 (both labeled in FIGS. 20 and 21) that are configured to guide at least one cutting instrument, such as a saw blade, to make a cut into a bone such as a tibia, femur, fibula, humerus, ulna, radius, or other bone. The osteotomy guide 500 can be configured to guide a cut into the bone adjacent to a joint, the cut dividing the bone into first and second bone segments, the first bone segment being closer to the joint. The cut can then be enlarged by pivoting the first segment of the patient's bone relative to the second segment of the bone so as to realign the bone. For example, the cut can be enlarged to realign the weight bearing line, to balance the pressure in the knee, although other alignment procedures are contemplated. The enlarged cut can then be fixed by attaching a bone plate that extends across the cut from the first bone segment to the second bone segment so as to affix the bone on opposed sides of the enlarged cut. For illustrative purposes, the guide 500 will be described and shown relative to its use in making a cut in a tibia.

Referring more specifically to FIGS. 16 to 19, the osteotomy guide 500 has an inner surface 502, and an outer surface 504 opposite the inner surface 502 with respect to an outward direction $D_o$. In other words, the inner surface 502 is opposite from the outer surface 504 with respect to an inward direction $D_i$, where the inward direction $D_i$ is opposite the outward direction $D_o$. The inner surface 502 can be a bone facing surface configured to face the bone. Preferably, at least a portion of the inner surface 502 is configured to contact the bone, and thus, can be considered to be a bone contacting surface. The inner surface 502 can be contoured so as to conform to a surface of the bone. The contour can be generally concave or can be any suitable contour to match the surface of the bone. The outer surface 504 can be configured to face away from the bone. In some examples, the outer surface 504 can be substantially convex, although embodiments of the disclosure are not so limited.

The osteotomy guide 500 has an anterior end 506, and a posterior end 508 opposite the anterior end 506 with respect to a posterior direction $D_{po}$. In other words, the anterior end 506 is opposite the posterior end 508 with respect to an anterior direction $D_a$, where the anterior direction $D_a$ and posterior direction $D_{po}$ are opposite one another. Note that, as used herein, the anterior and posterior directions $D_a$ and $D_{po}$ together may also be referred to as a transverse direction. The osteotomy guide 500 can be configured to be positioned on the bone such that the anterior end 506 is adjacent an anterior side of the bone and the posterior end 508 is adjacent a posterior side of the bone. However, it will be understood that osteotomy guide 500 can be otherwise positioned. The anterior direction $D_a$ and the posterior direction $D_{po}$ can be perpendicular to both the inward and outward directions $D_{in}$ and $D_o$.

The osteotomy guide 500 has a proximal end 510, and a distal end 512 opposite the proximal end 510 with respect to a distal direction $D_d$. In other words, the proximal end 510 is opposite the distal end 512 with respect to a proximal direction $D_{pr}$, where the proximal direction $D_{pr}$ and distal direction $D_d$ are opposite one another. The osteotomy guide 500 is configured to be positioned on the bone such that the proximal end 510 is oriented towards a proximal end of the bone, and the posterior end 512 is oriented towards a distal end the bone. The proximal direction $D_{pr}$ and distal direction $D_d$ can be perpendicular to the inward direction $D_{in}$, the outward direction $D_o$, the anterior direction $D_a$, and the posterior direction $D_{po}$.

The inner surface 502, and thus osteotomy guide 500, has at least two bone contacting regions that are configured to contact the bone when the osteotomy guide 500 is positioned along the bone. Each bone contacting region can be specifically sized and shaped to a contour of the bone of a particular patient. The at least two bone contacting regions can be arranged so as to define a gap 524 therebetween. The at least two bone contacting regions can include a first bone contacting region 518. The first bone contacting region 518 can be positioned closer to the anterior end 506 than a second bone contacting region 520 (discussed below). Thus, the first bone contacting region 518 may be considered to be an anterior bone contacting region. The first bone contacting region 518 can extend between the proximal end 510 and the distal end 512. For example, the first bone contacting region 518 can be elongate as it extends between the proximal end 510 and the distal end 512. At least a portion, up to an entirety, of the first bone contacting region 518 can be contoured as it extends in a direction between the anterior end 506 to the posterior end 508 so as to conform to the bone. The contour can be generally concave or can be any suitable contour to match the surface of the bone.

Additionally, or alternatively, the at least two bone contacting regions can include a second bone contacting region 520. The second bone contacting region 520 can be offset from the first bone contacting region 518 along the posterior direction $D_{po}$ so as to define a gap 524 therebetween. In other words, the first bone contacting region 518 can be offset from the second bone contacting region 520 along the anterior direction $D_a$ so as to define the gap 524 therebetween. The second bone contacting region 520 can be positioned closer to the posterior end 508 than the first bone contacting region 518. Thus, the second bone contacting region 520 may be considered to be a posterior bone contacting region. The second bone contacting region 520 can extend between the proximal end 510 and the distal end 512. For example, the second bone contacting region 520 can be elongate as it extends between the proximal end 510 and the distal end 512. At least a portion, up to an entirety, of the second bone contacting region 520 can be concave as it extends in a direction between the proximal end 510 and the distal end 512 so as to conform to the bone. The contour can be generally concave or can be any suitable contour to match the surface of the bone.

Additionally, or alternatively, the at least one bone facing surface can include a third bone contacting region 522. The third bone contacting region 522 can extend along the posterior direction $D_{po}$. The third bone contacting region 522 can be elongate as it extends along the posterior direction $D_{po}$. The third bone contacting region 522 can extend between the first bone contacting region 518 and the second bone contacting region 520. In one example, the third bone contacting region 522 can extend from the first bone contacting region 518 to at least the second bone contacting region 520, and in some examples, beyond the first bone contacting region 518. The third bone contacting region 522 can be disposed closer to the distal end 512 of the osteotomy guide 100 than the proximal end 510. Accordingly, the third bone contacting region 522 can be considered to be a second bone contacting region. The third bone contacting region 522 can be concave as it extends in a direction from the anterior end 506 towards the posterior end 508. The contour can be generally concave or can be any suitable contour to match the surface of the bone. A posterior end, such as a free end, of the third bone contacting region 522 can be configured (e.g., sized and shaped) to hook a holding point of the bone when the osteotomy guide 100 is affixed to the bone.

The at least two bone contacting regions can provide a better fit on the bone than one larger bone contacting surface. For example, the gap 524 between the first bone contacting region 518 and the second bone contacting region 520 can provide space for bony protrusions to extend between the first bone contacting region 518 and the second bone contacting region 520.

The osteotomy guide 500 can include an anterior body portion 526, and a posterior body portion 528 that is offset from the anterior body portion 526 along the posterior direction $D_{po}$. The anterior body portion 526 can at least partially define the anterior end 506 and can extend from the anterior end 506 towards the posterior end 508. The posterior body portion 528 can at least partially define the posterior end 508 and can extend from the posterior end 508 towards the anterior end 506. The anterior body portion 526 can include the first bone contacting region 518. The posterior body portion 528 can include the second bone contacting region 520. The osteotomy guide 500 can define a gap 524 between the first bone contacting region 518 and the second bone contacting region 520. The gap 524 can extend from the proximal end 510 towards the distal end 512. The gap 524 can extend towards and terminate at, for example, the third bone contacting region 522. The gap 524 can extend into the proximal end 510 such that the gap 524 is open at the proximal end 510; however, it will be understood that, in some embodiments, the gap 524 can be closed at the proximal end 510.

The gap 524 extends into the inner surface 502 towards the outer surface 504. At least a portion of the gap 524, such as a first portion, can extend through the outer surface 504. In other words, at least a first portion of the gap 524 can be open at the inner surface 502 and the outer surface 504. The first portion of the gap 524 can extend from the proximal end 510 towards the distal end 512. The first portion of the gap 524 can also extend from a posterior end of the gap 524 towards an anterior end of the gap 524 along the anterior direction $D_a$. A second portion of the gap 524 can terminate at the outer surface 504 such that the gap 524 is closed at the outer surface 504. The second portion can extend from the anterior end of the gap 524 towards the posterior end of the gap 524 along the posterior direction $D_{po}$, such as to the first portion. The second portion can also extend from a distal end of the gap 524 towards a proximal end of the gap 524, such as to the first portion. It will be understood that, the gap 524 can be alternatively configured. For example, an entirety of the gap 524 can be open at the outer surface 504 or closed at the outer surface 504. Alternatively, the first and second portions of the gap 524 can have configurations other than that shown.

Referring to FIGS. 20 and 21, in embodiments where the gap 524 extends through the inner surface 502 and the outer surface 504, the osteotomy guide 500 can include a first arm 530, and a second arm 532 that is offset from the first arm 530 with respect to the posterior direction $D_{po}$. The first arm 530 and the second arm 532 can be separated from one another by the gap 524. The anterior body portion 526 can include the first arm 530. The first arm 530 can include the first bone contacting region 518. The posterior body portion 528 can include the second arm 532. The second arm 532 can include the second bone contacting region 520. The second arm 532 can extend between the posterior end 508 and the gap 524. The second arm 532 can extend from the proximal end 510 towards the distal end 512. The second arm 532 can include an edge 533 that can be used to verify correct positioning of the osteotomy guide 500. The edge 533 can at least partially define the gap 524. The edge 533 can extend along a direction that extends from the proximal end 510 towards the distal end 512. The edge 533 can be configured to abut the bone when the osteotomy guide 500 is properly positioned along the bone. The edge 533 can be configured to be viewed through the gap 524 to verify that the edge 533 abuts the bone and no space exists between the edge 533 and the bone.

With continued reference to FIGS. 20 and 21, the osteotomy guide 500 can have at least one ascending guide surface that is configured to guide the cutting instrument to make an ascending cut into the bone. However, it will be understood that, in alternative embodiments, the guide 100 can be devoid of an ascending guide surface. The ascending cut may be made, for example, around the tibial tuberosity behind the patellar tendon. Thus, the osteotomy guide 500 can be configured (e.g., sized and shaped) such that each of the at least one ascending guide surface is aligned with the tibial tuberosity when the osteotomy guide 500 is affixed to the bone. Each of the at least one ascending guide surface can be disposed at the anterior end 506 of the osteotomy guide 500.

The at least one ascending guide surface can include a first ascending guide surface 534. The first ascending guide surface 534 can extend along an ascending axis AA that extends along an ascending direction so as to at least partially define an ascending cutting path into the bone. The ascending direction is angularly offset with respect to the proximal direction $D_{pr}$ and the transverse direction (e.g., the anterior and posterior directions $D_a$ and $D_{po}$). For example, the ascending direction can extend at an angle that is between the proximal direction $D_{pr}$ and the transverse direction. Thus, the first ascending guide surface 534 can be angled towards the anterior direction $D_a$ as the first ascending guide surface 534 extends towards the proximal end 510. The first arm 530 can define the first ascending guide surface 534.

In some embodiments, the at least one ascending guide surface can include a second ascending guide surface 536 that is offset from the first ascending guide surface 534 so as to define an ascending groove 514 therebetween. The second ascending guide surface 536 can extend along an ascending axis AA that extends along the ascending direction so as to at least partially define an ascending cutting path into the bone. Thus, the second ascending guide surface 536 can be angled towards the anterior direction $D_a$ as the second ascending guide surface 534 extends towards the proximal end 510. At least a portion of the first ascending guide surface 534 can face the second ascending guide surface 536 so as to define the ascending groove 514 therebetween. The ascending groove 514 can be configured to guide a cutting instrument to make an ascending cut into the bone. In some embodiments, the second ascending guide surface 536 can be substantially parallel to the first ascending guide surface 534. The first ascending guide surface 534 can have a length along the ascending direction that is greater than that of the second ascending guide surface 536, although embodiments of the disclosure are not so limited.

In embodiments having the second ascending guide surface 536, the osteotomy guide 500 can include an ascending leg 535 that defines the second ascending guide surface 536. The ascending leg 535 can have a first end that is attached to the anterior body portion 526 at a bridge 537, and a second end that is offset from the first end along the ascending direction. The ascending leg 535 can be integral and monolithic with the anterior body portion 526, although embodiments of the disclosure are not so limited. The second end can be a free end that is free from attachment to the anterior body portion 526 or any other portion of osteotomy guide 500. The ascending groove 514 can extend into osteotomy guide 500 along a descending direction opposite the ascending direction. As such, a proximal end of the ascending groove 514 can be open, and a distal end of the ascending groove 516 can be closed, where the distal end is offset from the proximal end along the descending direction. It will be understood that, in alternative embodiments, the ascending groove 514 can terminate adjacent to the first end or can be open at both the first and second ends.

The osteotomy guide 500 can have at least one transverse guide surface that is configured to guide a cutting instrument to make a transverse cut into the bone. Each transverse guide surface can be disposed at the distal end 512 of the osteotomy guide 500. Each transverse guide surface can be offset from the gap 524 with respect to the distal direction $D_o$. For example, each transverse guide surface can be offset from the third bone contacting region 522 with respect to the distal direction $D_o$.

The at least one transverse guide surface can include a first transverse guide surface 538. The first transverse guide surface 538 can extend along a transverse axis $A_T$ that extends along the anterior direction $D_a$ and the posterior direction $D_{po}$ (herein, collectively referred to as the transverse direction) so as to at least partially define a transverse cutting path into the bone. The ascending axis AA and transverse axis $A_T$ can intersect one another.

In some embodiments, the at least one transverse guide surface can include a second transverse guide surface 540 that is offset from the first transverse guide surface 538 so as to define a transverse groove 516 therebetween that extends along the transverse axis. The second transverse guide surface 540 can extend along the transverse axis $A_T$ that extends along the transverse direction. At least a portion of the first transverse guide surface 538 can face the second transverse guide surface 540 so as to define the transverse groove 516 therebetween. The transverse groove 516 can be configured to guide a cutting instrument to make a transverse cut into the bone. The cutting instrument may be the same as, or different from, the cutting instrument used to make the ascending cut. In some embodiments, the second transverse guide surface 540 can be substantially parallel to the first transverse guide surface 538. The first transverse guide surface 538 can have a length along the posterior direction $D_{po}$ that is greater than that of the second transverse guide surface 540, although embodiments of the disclosure are not so limited.

In embodiments having the second transverse guide surface 540, osteotomy guide 500 can include a transverse leg 539 that defines the second transverse guide surface 540. The transverse leg 539 can have a first end that is attached to the anterior body portion 526, and a second end that is offset from the first end along the posterior direction $D_{po}$. The transverse leg 539 can be integral and monolithic with the anterior body portion 526, although embodiments of the disclosure are not so limited. The second end can be a free end that is free from attachment to the anterior body portion 526 or any other portion of the osteotomy guide 500. The transverse groove 516 can extend into the osteotomy guide 500 along the anterior direction $D_a$. As such, a posterior end of the transverse groove 516 can be open, and an anterior end of the transverse groove 516 can be closed, where the posterior end is offset from the anterior end along the posterior direction $D_{po}$. It will be understood that, in alternative embodiments, the transverse groove 516 can terminate adjacent to the first end or can be open at both the first and second ends.

The transverse leg 539 can have an edge 541 that can be used to verify correct positioning of the osteotomy guide 500. The edge 541 can at least partially define a distal-most edge of the guide 500. The edge 541 can extend along the transverse direction between the anterior end 606 and the posterior end 508. The edge 541 can be configured to abut the bone when the osteotomy guide 500 is properly positioned along the bone. Proper positioning of the guide 500 can be verified by verifying that the edge 541 abuts the bone and no space exists between the edge 541 and the bone.

As can be seen in FIGS. 20 and 21, the bridge 537 separates the ascending groove 514 from the transverse groove 516. As such, when the ascending cut and transverse cut are made in the bone, the bridge 537 can obstruct the cutting of the segment of the bone that joins the ascending cut and transverse cut and that underlies the bridge 537. In this example, the bridge 537 obstructs the ascending cut. Thus, the first ascending guide surface 534, and consequently the ascending cutting groove 514, terminates such that it does not intersect the transverse cutting groove 516. As such, the ascending cut may need to be extended after the osteotomy guide 500 is removed so as to join the ascending cut to the transverse cut. Extending the ascending cut may be easier than extending the transverse cut because the distance through which the ascending cut extends into the bone may be less than the distance into which the transverse cut extends into the bone. To accommodate such cutting, the first transverse guide surface 540 can extend at least up to, and in some embodiments beyond, the first ascending guide surface 534 with respect to the posterior direction $D_{po}$. In other words, the first transverse guide surface 540 be intersected by a plane that is defined by the first ascending guide surface 534. In embodiments that employ first and second transverse guide surfaces 538 and 540, the plane that is defined by the first ascending guide surface 534 can intersect the transverse groove 516.

The osteotomy guide 500 can define at least one fixation hole that extends through the osteotomy guide 500. Each fixation hole can be configured to receive a fixation pin, such as a Kirschner wire, therethrough so as to affix the osteotomy guide 500 to the bone. Each fixation hole can extend through the inner surface 502 and the outer surface 504 of the osteotomy guide 500. It will be understood that the locations of the fixation holes can vary from the embodiment shown.

In one example, the at least one fixation hole can include a proximal fixation hole 542. The proximal fixation hole 542 can extend through the first arm 530 adjacent the proximal end 510 of the osteotomy guide 500. The osteotomy guide 500 can include a neck 544 that extends from the anterior body portion 526 along the proximal direction $D_{pr}$. The proximal fixation hole 542 can extend through the neck 544. The proximal fixation hole 542 can correspond to a location of a hole of the bone fixation plate that is to be affixed to the bone. Thus, proximal fixation hole 542 can act as a guide for forming a hole in the bone that is used for both (i) a fixation pin that secures the osteotomy guide 500 to the bone and (ii) a bone anchor that affixes the bone fixation plate to the bone after the cut in the bone has been enlarged.

The at least one fixation hole can include at least one, such as two, distal bone fixation holes 546 and 548. Each distal bone fixation hole 546 and 548 can be offset from the proximal bone fixation hole 542 with respect to the distal direction $D_d$. Each distal bone fixation hole 546 and 548 can extend through the osteotomy guide 500 at a position adjacent to the first transverse guide surface 538 and transverse groove 516. In some embodiments, each distal bone fixation hole 546 and 548 can be open at the first transverse guide surface 538, such as open to the transverse groove 516. In embodiments having first and second distal bone fixation holes 546 and 548, the first distal bone fixation hole 546 can be spaced from the second distal bone fixation hole 548 along the anterior direction $D_a$. The first and second distal bone fixation holes 546 and 548 can be aligned along a direction that is substantially parallel with the first transverse guide surface 538.

The osteotomy guide 500 can be a unitary body having the first arm 530, the second arm 532, the ascending leg 535, and the transverse leg 539. In one example, the osteotomy guide 500 can be 3-D printed as a single monolithic body. Forming the osteotomy guide 500 as a single monolithic body can limit costs of 3-D printing the osteotomy guide 500 and can simplify the manufacturing process. In alternative embodiments, various components of the osteotomy guide 500 can be affixed, such as glued, welded, fastened, or otherwise coupled to, one another. Providing the osteotomy guide 500 as a unitary body can simplify handling of the osteotomy guide 500 and improve cutting accuracy over conventional guides that include two or more movable parts where stability of the movable parts can be difficult to maintain.

In one embodiment, a method of fabricating the osteotomy guide 500 can include obtaining a 3-D computer model of the patient's anatomy. This obtaining step can comprise receiving the 3-D computer model in a computer. Additionally, or alternatively, this obtaining step can comprise obtaining at least one image, such as a plurality of images, of the patient's anatomy using an imaging machine, such as a CT or MRI scan, and generating the 3-D computer model of the patient's anatomy from the image. The method can comprise a step of generating a 3-D computer model of the osteotomy guide 500 that conforms to the patient's anatomy. The method can comprise a step of 3-D printing the osteotomy guide 500 based on the 3-D computer model of the osteotomy guide 500.

The osteotomy guide 500 can include one or more push positions that are configured to be pressed by a medical professional when positioning the guide 500 against the bone so as to properly align a position of the guide 500 on the bone. For example, the osteotomy guide 500 can include a first push position 531 that can be pressed by a medical professional when positioning the guide 500 against the bone so as to properly align a position of the guide 500 along the proximal and distal directions $D_{pr}$ and $D_d$. The second arm 532 can define the first push position 531. The first push position 531 can be defined as a tab. The first push position 531 can include indicia that indicates the first push position 531. For example, the first push position 531 can include ridges that extend out from the outer surface 504 of the guide 500. In one such example, the ridges can include circular or oval ridges that are concentric. It will be understood that indicia other than ridges are contemplated, including indicia that does not protrude from the outer surface 504.

Additionally, or alternatively, the osteotomy guide 500 can include a second push position 543 that can be pressed by a medical professional when positioning the guide 500 against the bone so as to properly align a position of the guide 500 along the anterior and posterior directions $D_a$ and $D_p$. The second push position 543 can be offset from the first push position 531 with respect to the distal direction $D_d$. The second push position 543 can be offset from the first push position 531 with respect to the anterior direction $D_a$. The second push position 543 can be offset from the first push position 531 with respect to the outward direction $D_o$. The second push position 543 can be defined as a tab. The second push position 543 can include indicia that indicates the second push position 543. For example, the second push position 543 can include ridges that extend out from the outer surface 504 of the guide 500. In one such example, the ridges can include circular or oval ridges that are concentric. It will be understood that indicia other than ridges are contemplated, including indicia that does not protrude from the outer surface 504.

A surgical method that employs the osteotomy guide 500 of FIGS. 16 to 24 can be implemented in a manner similar to that of the method of FIGS. 9 to 14, with a few notable differences. In the alignment step 404, the medical professional can press at least one of (i) the first push position 531 so as to properly position the guide 500 along the proximal and distal directions $D_{pr}$ and $D_d$, and (ii) the second push position 543 so as to properly position the guide 500 along the anterior and posterior directions $D_a$ and $D_{po}$. In the verifying step 408, the medical professional can verify that the edges 533 and 541 abut and conform to the bone such that no spaces exist between the edge 533 and the bone or between the edge 541 and the bone. The enlarging step 416 can comprise using a cutting instrument, such as a chisel or saw, to further enlarge the ascending portion of the cut, rather than the transverse portion, thereby extending the ascending portion of the cut to the transverse portion of the cut.

Turning now to FIGS. 25 to 34, an osteotomy guide 600 is shown according to another embodiment. The osteotomy guide 600 is configured to guide at least one cutting instrument to make a cut into a bone for an osteotomy procedure. The osteotomy guide 600 can be custom constructed to conform to a bone of a specific patient. In other words, the osteotomy guide 600 may be patient specific. The osteotomy guide 600 can be three-dimensionally (3-D) printed or can be fabricated in any other suitable manner. In at least some embodiments, the osteotomy guide 600 can include a one-piece body. The osteotomy guide 600 defines at least one ascending guide surface 634 and at least one transverse guide surface 638 (both labeled in FIGS. 29 and 30) that are configured to guide at least one cutting instrument, such as a saw blade, to make a cut into a bone such as a tibia, femur, fibula, humerus, ulna, radius, or other bone. The osteotomy guide 600 can be configured to guide a cut into the bone adjacent to a joint, the cut dividing the bone into first and second bone segments, the first bone segment being closer to the joint. The cut can then be enlarged by pivoting the first segment of the patient's bone relative to the second segment of the bone so as to realign the bone. For example, the cut can be enlarged to realign the weight bearing line, to balance the pressure in the knee, although other alignment procedures are contemplated. The enlarged cut can then be fixed by attaching a bone plate that extends across the cut from the first bone segment to the second bone segment so as to affix the bone on opposed sides of the enlarged cut. For illustrative purposes, the guide 600 will be described and shown relative to its use in making a cut in a tibia.

Referring more specifically to FIGS. 25 to 28, the osteotomy guide 600 has an inner surface 602, and an outer surface 604 opposite the inner surface 602 with respect to an outward direction $D_o$. In other words, the inner surface 602 is opposite from the outer surface 604 with respect to an inward direction $D_i$, where the inward direction $D_i$ is opposite the outward direction $D_o$. The inner surface 602 can be a bone facing surface configured to face the bone. At least a portion of the inner surface 602 is configured to contact the bone, and thus, can be considered to be a bone contacting surface. Thus, the inner surface 602 can have at least one bone contacting region 618 that is contoured so as to conform to a surface of the bone. The contour can be generally concave or can be any suitable contour to match the surface of the bone. In alternative embodiments (not shown), the inner surface 602 can have at least two bone contacting regions in a manner similar to that described above with respect to FIGS. 1 to 15 and FIGS. 16 to 24. The outer surface 604 can be configured to face away from the bone. In some examples, the outer surface 604 can be substantially convex, although embodiments of the disclosure are not so limited.

The osteotomy guide 600 has an anterior end 606, and a posterior end 608 opposite the anterior end 606 with respect to a posterior direction $D_{po}$. In other words, the anterior end 606 is opposite the posterior end 608 with respect to an anterior direction $D_a$, where the anterior direction $D_a$ and posterior direction $D_{po}$ are opposite one another. Note that, as used herein, the anterior and posterior directions $D_a$ and $D_{po}$ together may also be referred to as a transverse direction. The osteotomy guide 600 can be configured to be positioned on the bone such that the anterior end 606 is adjacent an anterior side of the bone and the posterior end 608 is adjacent a posterior side of the bone. However, it will be understood that osteotomy guide 600 can be otherwise positioned. The anterior direction $D_a$ and the posterior direction $D_{po}$ can be perpendicular to both the inward and outward directions $D_{in}$ and $D_o$.

The osteotomy guide 600 has a proximal end 610, and a distal end 612 opposite the proximal end 610 with respect to a distal direction $D_d$. In other words, the proximal end 610 is opposite the distal end 612 with respect to a proximal direction $D_{pr}$, where the proximal direction $D_{pr}$ and distal direction $D_d$ are opposite one another. The osteotomy guide 600 can include a proximal body portion 626, and a distal body portion 628 that is offset from the proximal body portion 626 along the distal direction $D_d$. The distal body portion 628 can include the at least one bone contacting region 618 of the inner surface 602. The osteotomy guide 600 is configured to be positioned on the bone such that the proximal end 610 is oriented towards a proximal end of the bone, and the posterior end 612 is oriented towards a distal end the bone. The proximal direction $D_{pr}$ and distal direction $D_d$ can be perpendicular to the inward direction $D_{in}$, the outward direction $D_o$, the anterior direction $D_a$, and the posterior direction $D_{po}$.

With reference to FIGS. 29 and 30, the osteotomy guide 600 can have at least one ascending guide surface that is configured to guide the cutting instrument along an ascending cutting path to make an ascending cut into the bone. However, it will be understood that, in alternative embodiments, the guide 100 can be devoid of an ascending guide surface. The ascending cut may be made, for example, around the tibial tuberosity behind the patellar tendon. Thus, the osteotomy guide 600 can be configured (e.g., sized and shaped) such that each of the at least one ascending guide surface is aligned with the tibial tuberosity when the osteotomy guide 600 is affixed to the bone. Each of the at least one ascending guide surface can be disposed at the anterior end 606 of the osteotomy guide 600. The at least one ascending guide surface can include a first ascending guide surface 634. The first ascending guide surface 634 can extend along an ascending direction that is angularly offset with respect to the proximal direction $D_{pr}$ and the transverse direction (e.g., the anterior and posterior directions $D_a$ and $D_{po}$). For example, the ascending direction can extend at an angle that is between the proximal direction $D_{pr}$ and the transverse direction. Thus, the first ascending guide surface 634 can be angled towards the anterior direction $D_a$ as the first ascending guide surface 634 extends towards the proximal end 610. The distal body portion 628 can define the first ascending guide surface 634. In alternative embodiments (not shown), the at least one ascending guide surface can include a second ascending guide surface that is offset from the first ascending guide surface 634 so as to define an ascending groove therebetween in a manner similar to that described above.

The osteotomy guide 600 can have at least one transverse guide surface that is configured to guide a cutting instrument along a transverse cutting path to make a transverse cut into the bone. Each transverse guide surface can be disposed at the distal end 612 of the osteotomy guide 600. The at least one transverse guide surface can include a first transverse guide surface 638. The first transverse guide surface 638 can extend along the anterior direction $D_a$ and the posterior direction $D_{po}$ (herein, collectively referred to as the transverse direction) so as to at least partially define a transverse cutting path into the bone. At least one of the ascending and transverse cutting paths can intersect the other. The distal body portion 628 can define the first transverse guide surface 638. In alternative embodiments (not shown), the at least one transverse guide surface can include a second transverse guide surface that is offset from the first transverse guide surface 638 so as to define a transverse groove therebetween in a manner similar to that discussed above.

The osteotomy guide 600 can define at least one fixation hole that extends through the osteotomy guide 600. Each fixation hole can be configured to receive a fixation pin, such as a Kirschner wire, therethrough so as to affix the osteotomy guide 600 to the bone. Each fixation hole can extend through the inner surface 602 and the outer surface 604 of the osteotomy guide 600. It will be understood that the locations of the fixation holes can vary from the embodiment shown.

In one example, the at least one fixation hole can include a proximal fixation hole 642. The osteotomy guide 600, such as the proximal body portion 626, can include a neck 644 that extends from the distal body portion 628 along the proximal direction $D_{pr}$. The proximal fixation hole 642 can extend through the neck 644. The neck 644 can have an inner surface 645 that is configured to face the bone. The inner surface 645 of the neck 644 can be offset with respect to the at least one bone contacting surface 618 with respect to the outward direction $D_O$. Consequently, when the bone facing surface 618 is aligned with the bone, the inner surface 645 of the neck 644 can be spaced from the bone so as to accommodate soft tissue between the inner surface 645 and the bone. Further, the proximal fixation hole 642 can correspond to a location of a hole of the bone fixation plate that is to be affixed to the bone. Thus, proximal fixation hole 642 can act as a guide for forming a hole in the bone that is used for both (i) a fixation pin that secures the osteotomy guide 600 to the bone and (ii) a bone anchor that affixes the bone fixation plate to the bone after the cut in the bone has been enlarged.

The at least one fixation hole can include at least one, such as two, distal bone fixation holes 646 and 648. Each distal bone fixation hole 646 and 648 can be offset from the proximal bone fixation hole 642 with respect to the distal direction $D_d$. Each distal bone fixation hole 646 and 648 can extend through the osteotomy guide 600, such as through the distal body portion 628. In embodiments having first and second distal bone fixation holes 646 and 648, the first distal bone fixation hole 646 can be spaced from the second distal bone fixation hole 648 along the anterior direction $D_a$. The first and second distal bone fixation holes 646 and 648 can be aligned along a direction that is substantially parallel with the first transverse guide surface 638.

With reference to FIGS. 29, 30, 33, and 34, the osteotomy guide 600 can include an alignment guide 650 that is configured to aid in re-alignment of the first and second bone segments (e.g., 300a and 300b in FIG. 34) once the cut divides the bone into first and second bone segments. For example, the alignment guide 650 can include an arm that extends away from the distal body portion 628 along the distal direction $D_d$, although the alignment guide 650 can be configured in a manner other than an arm. The alignment guide 650 can extend from the distal body portion 628 adjacent the anterior end 606 of the guide 600. The alignment guide 650 can be offset from the inner surface 602 with respect to the outward direction $D_o$ such that a cutting instrument can be inserted between the alignment guide 650 and the bone so as to cut the bone at a position that underlies the alignment guide 650 while the osteotomy guide 600 is attached to the bone, thereby allowing the transverse and ascending cuts to be joined without removing the osteotomy guide 600.

The alignment guide 650 can define an opening 654 therethrough that extends along the inner and outer directions $D_i$ and $D_o$. The opening 654 can be configured to receive an alignment member 212, such as a Kirshner wire, a shaft, a bar, or any other suitable member. The alignment guide 650 is configured such that, when the osteotomy guide 600 is attached to the first bone segment 300a and the alignment member 212 is received in the opening 654, the alignment member 212 abuts an inner surface of the second bone segment 300b when the first bone segment 300a is moved to affect the desired realignment of the bone. The inner surface of the second bone segment 300b can be the surface of the second bone segment 300b that is formed by the transverse cut 310. Desired alignment of the first bone segment 300a can be determined by moving the first bone segment 300a so as to enlarge the osteotomy cut 307 until the alignment member 212 abuts the inner surface of the second bone segment 300b. It will be understood that, although not shown, the embodiments of FIGS. 1 to 24 can have an alignment guide configured in the same manner as the alignment guide 650.

The osteotomy guide 600 can be a unitary body having the proximal body portion 626, the distal body portion 628, and the alignment guide 650. In one example, the osteotomy guide 600 can be 3-D printed as a single monolithic body. Forming the osteotomy guide 600 as a single monolithic body can limit costs of 3-D printing the osteotomy guide 600 and can simplify the manufacturing process. In alternative embodiments, various components of the osteotomy guide 600 can be affixed, such as glued, welded, fastened, or otherwise coupled to, one another. Providing the osteotomy guide 600 as a unitary body can simplify handling of the osteotomy guide 600 and improve cutting accuracy over conventional guides that include two or more movable parts where stability of the movable parts can be difficult to maintain.

In one embodiment, a method of fabricating the osteotomy guide 600 can include obtaining a 3-D computer model of the patient's anatomy. This obtaining step can comprise receiving the 3-D computer model in a computer. Additionally, or alternatively, this obtaining step can comprise obtaining an image of the patient's anatomy using an imaging machine, and generating the 3-D computer model of the patient's anatomy from the image. The method can comprise a step of generating a 3-D computer model of the osteotomy guide 600 that conforms to the patient's anatomy. The method can comprise a step of 3-D printing the osteotomy guide 600 based on the 3-D computer model of the osteotomy guide 600.

A surgical method that employs the osteotomy guide 600 of FIGS. 25 to 34 can be implemented in a manner similar to that of the method of FIGS. 9 to 14, with a few notable differences. In the cutting steps 410 and 412, the cutting instrument can be passed under the alignment guide 650 so as to cut into the bone to join the ascending and transverse cuts. The step 414 of removing the osteotomy guide can be omitted, and the enlarging step 416 can be performed with the osteotomy guide 600 attached to the bone 300. In so doing, a distractor instrument (not shown) can be used to enlarge the cut 307 in step 416 until the alignment member 212 abuts the inner surface of the second bone segment 300b. After enlarging the cut 307, the distractor instrument can maintain the first and second bone segments 300a and 300b in the desired relative positions while the osteotomy guide 600 is removed, and the plate is affixed in step 418.

Turning now to FIGS. 35 to 41, a spacer 700 is shown according to one embodiment. At least a portion of the spacer 700 is configured to be received in the osteotomy cut 307 in the bone between the first bone segment 300a and the second bone segment 300b so as to provide a desired spacing between the first and second bone segments 300a and 300b. The spacer 700 can be inserted into the osteotomy cut 307 after the transverse cut 310 and ascending cut 308 has been made (e.g., in step 416 of FIG. 9 above). The spacer 700 has a first end 702 and a second end 704 that are opposite one another along a first direction $D_1$. The spacer 700 can have a handle portion 706 and a wedge portion 708. The handle portion 706 can extend from the first end 702 towards the second end 704, such as to the wedge portion 708. The handle portion 706 can have any suitable shape for grasping by a medical professional. For example, the handle portion 706 can have a substantially cylindrical shape.

The wedge portion 708 can extend from the second end 704 towards the first end 702, such as to the handle portion 706. The wedge portion 708 can have a first bone facing surface 710 and a second bone facing surface 712 that are opposite one another with respect to a second direction $D_2$, perpendicular to the first direction $D_1$. The first and second bone facing surfaces 710 and 712 can taper towards one another as they extend in the first direction $D_1$ towards the second end 704. The first and second bone facing surfaces 712 can be configured to engage opposing surfaces of the first and second bone segments 300a and 300b so as to space the first and second bone segments 300a and 300b from one another.

The wedge portion 708 can have a first side 714 and a second side 716 that are opposite from one another along a third direction $D_3$. The first and second sides 714 and 716 can extend between the first and second bone facing surfaces 710 and 712. The second side 716 can taper towards the first side 714 as the second side 716 extends along the first direction $D_1$ towards the first end 702. In one example, the second side 716 can curve towards the first side 714 as the second side 716 extends along the first direction $D_1$ towards the first end 702. The curvature of the second side 716 can conform to a curvature of the bone when the wedge portion 708 is seated in the cut 307 in the bone 300. The first side 714 can be substantially planar or can have any other suitable shape.

Figure 41:
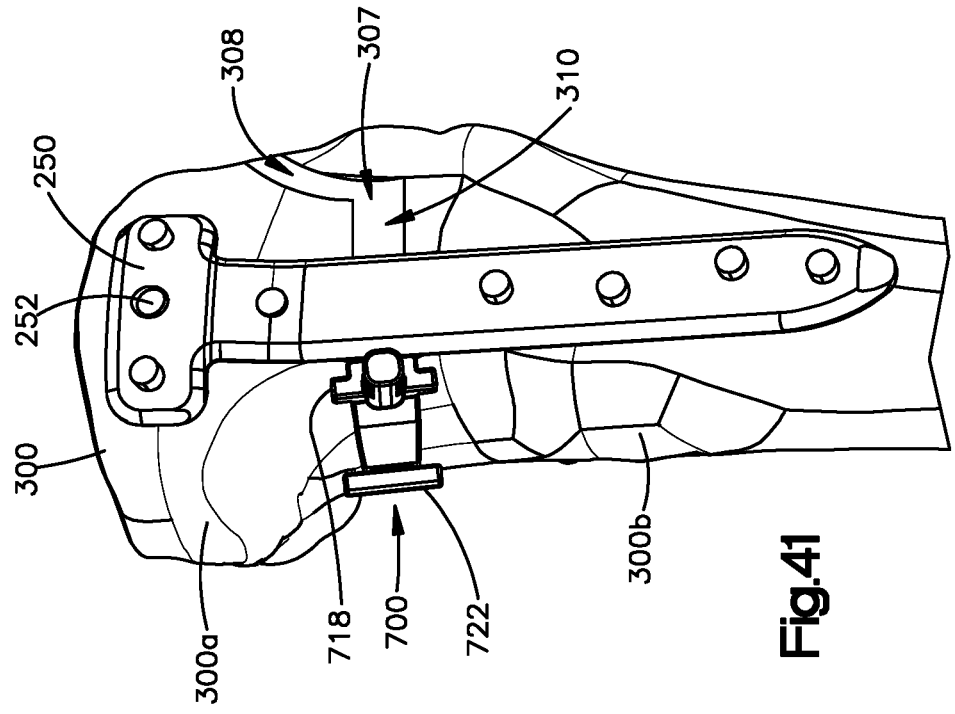
FIG. 41 shows a second perspective view of a tibia with the spacer of FIG. 35 implanted into an osteotomy cut in the tibia and with a bone fixation plate attached to the tibia.
Figure 40:
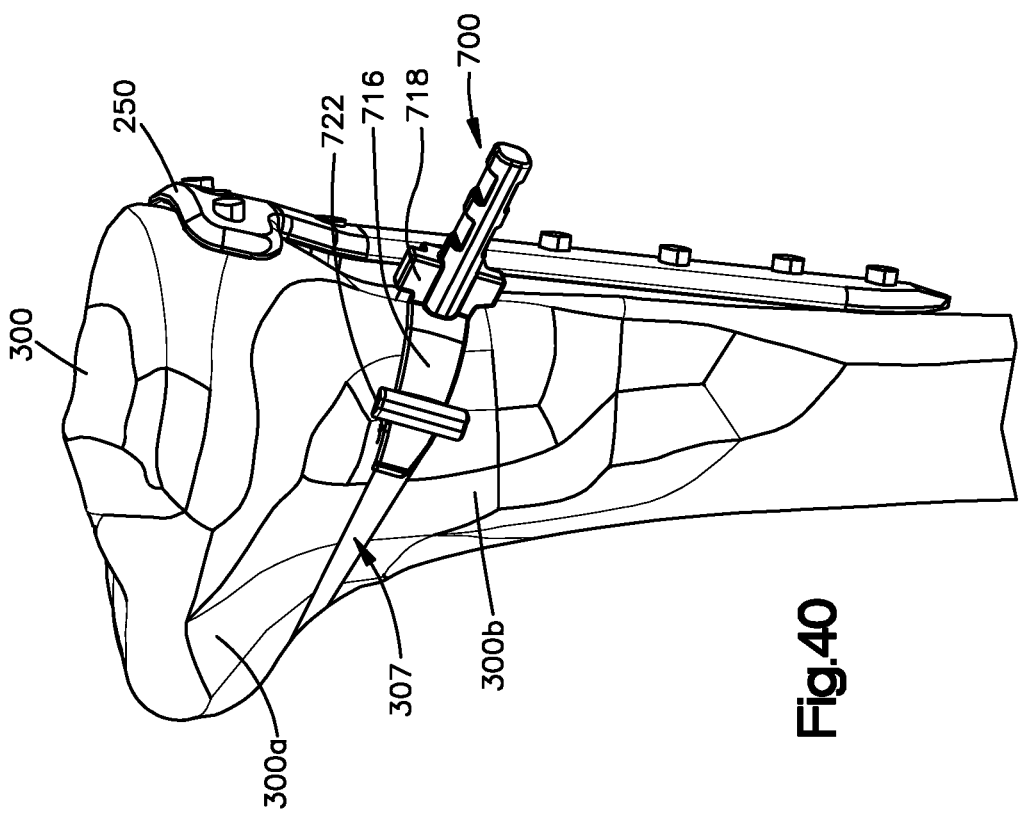
FIG. 40 shows a first perspective view of a tibia with the spacer of FIG. 35 implanted into an osteotomy cut in the tibia and with a bone plate attached to the tibia.
Figure 42:
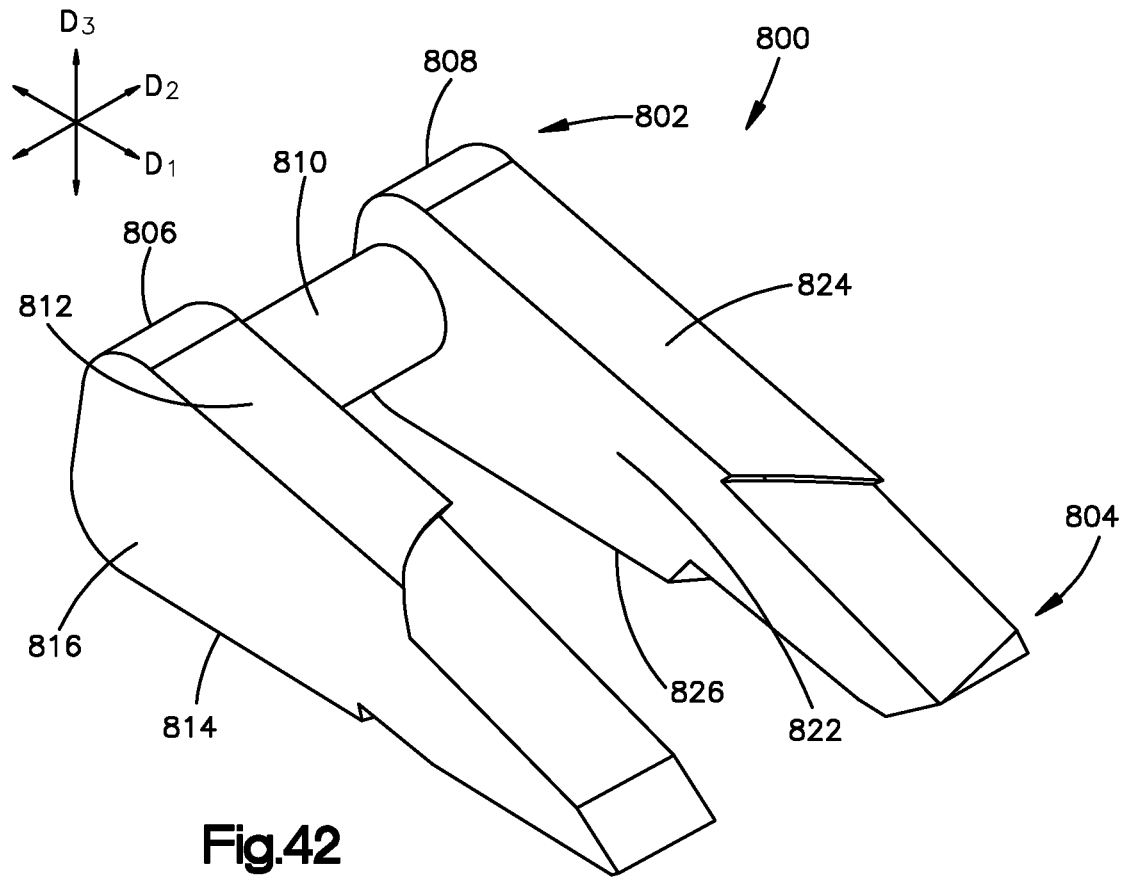
FIG. 42 shows a first perspective view of a spacer according to another embodiment.
Figure 43:
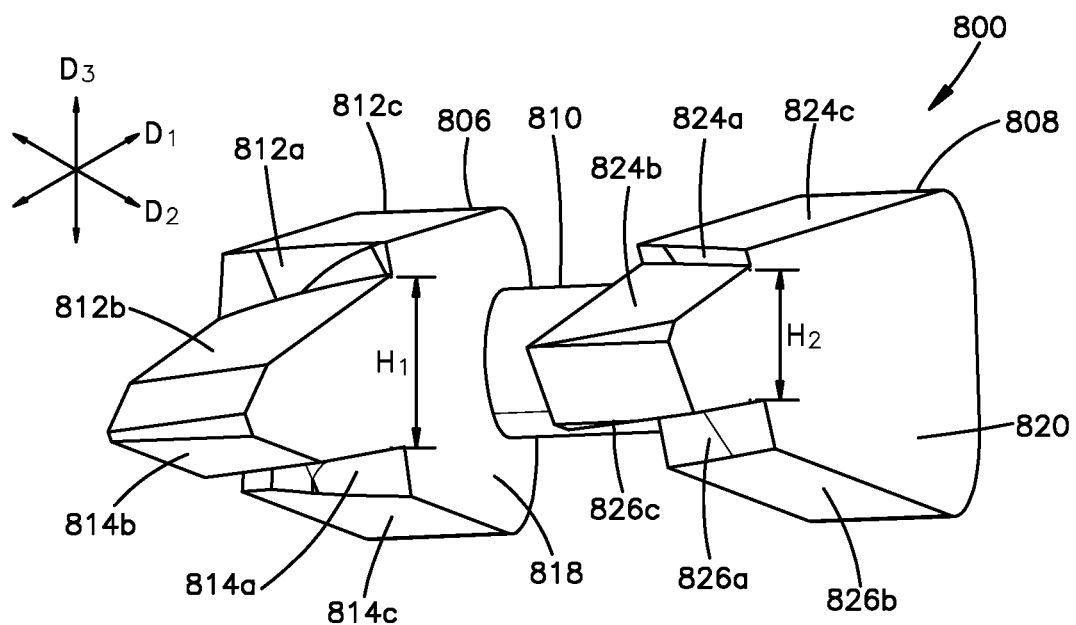
FIG. 43 shows a second perspective view of the spacer of FIG. 42.
Figures 44, 45:
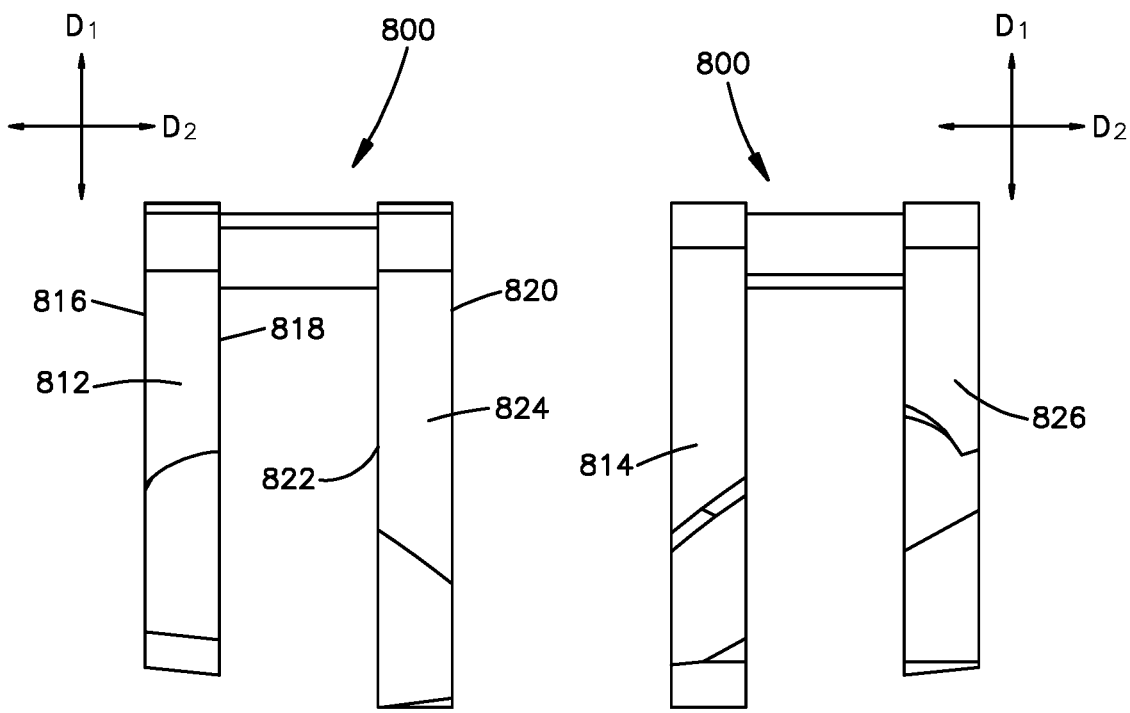
FIG. 44 shows a plan view of a top of the spacer of FIG. 42.
FIG. 45 shows a plan view of a bottom of the spacer of FIG. 42.
Figure 46:
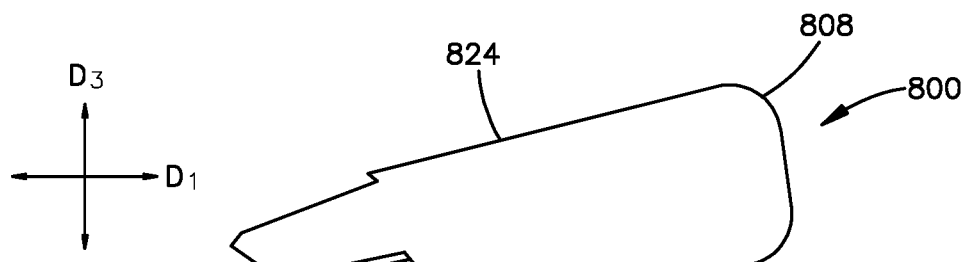
FIG. 46 shows an elevation view of one side of the spacer of FIG. 42.
Figure 47:
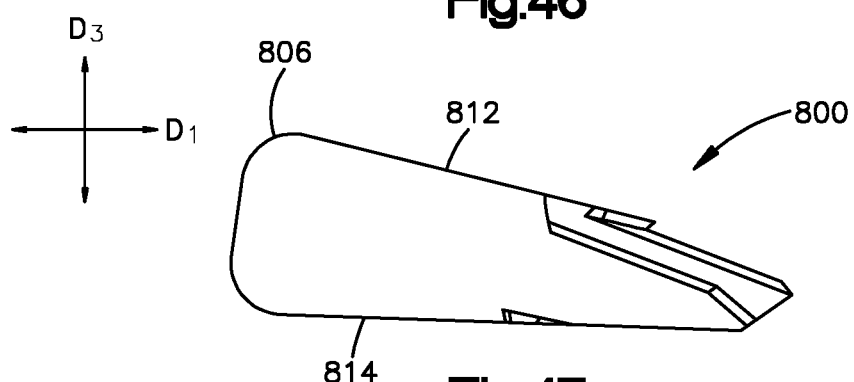
FIG. 47 shows an elevation view of another side of the spacer of FIG. 42.

The spacer 700 can include at least one stop that is configured to limit an insertion depth of the spacer 700 into the bone 300. For example, the spacer 700 can include a first stop 718 that is configured to limit translation of the spacer 700 into the bone 300 along the first direction $D_1$. The first stop 718 can be supported at a proximal end of the wedge portion 708. The first stop 718 can have a width along the second direction $D_2$ that is greater than a width of the wedge portion 708 along the second direction $D_2$. The first stop 718 can extend outwardly relative to at least one, such as both, of the first and second bone facing surfaces 710 and 712 with respect to the second direction $D_2$. The first stop 718 can define at least one shoulder 720, such as a pair of shoulders 720, each shoulder 720 configured to rest on the bone 300 when the spacer 700 is received in the cut 307 as shown in FIG. 40. Each shoulder 720 can face in a direction (e.g., the first direction $D_1$) that extends towards the second end 704. The first side 714 and/or first stop 718 can be configured such that the bone fixation plate 250 abuts the first stop 718 as shown in FIG. 41 when the first stop 718 is received in the cut 307 so as to properly align the bone fixation plate 250 along the bone 300.

Additionally, or alternatively, the spacer 700 can include a second stop 722 that is configured to limit rotation of the spacer 700 relative to the bone 300 along an axis that extends along the second direction $D_2$. The second stop 722 can be supported by the wedge portion 708. For example, the second stop 722 can be supported along the second side 716 between the handle 706 and the second end 704 of the spacer 700. The second stop 722 can project outwardly from the second side 716 with respect to the third direction $D_3$. The second stop 722 can have a width along the second direction $D_2$ that is greater than a width of the wedge portion 708 along the second direction $D_2$. The second stop 722 can extend outwardly relative to at least one, such as both, of the first and second bone facing surfaces 710 and 712 with respect to the second direction $D_2$. The second stop 722 can define at least one shoulder 724, such as a pair of shoulders 724, each shoulder 724 configured to rest on the bone 300 when the spacer 700 is received in the cut 307 as shown in FIGS. 40 and 41. Each shoulder 724 can face in a direction (e.g., the second direction $D_2$) that extends towards the first side 714. The spacer 700 is configured such that, when the second stop 722 abuts the bone 300, the stop 722 restricts rotation of the spacer 700 into the cut 706 about an axis that extends along the second direction $D_2$.

Turning now to FIGS. 42 to 49, a spacer 800 is shown according to another embodiment. At least a portion of the spacer 800 is configured to be received in the cut 307 in the bone between the first bone segment 300a and the second bone segment 300b so as to provide a desired spacing between the first and second bone segments 300a and 300b. The spacer 800 can be inserted into the osteotomy cut 307 after the transverse cut 310 and ascending cut 308 has been made (e.g., in step 416 of FIG. 9 above). The spacer 800 has a first end 802 and a second end 804 that are opposite one another along a first direction $D_1$. The spacer 800 has a first wedge portion 806 and a second wedge portion 808 that are offset from one another along a second direction $D_2$, perpendicular to the first direction $D_1$. In at least some embodiments, the first wedge portion 806 can be spaced from the second wedge portion 808 so as to define a space between the first and second wedge portions 806 and 808 along the second direction $D_2$. The spacer 800 can have a connector 810 that connects the first and second wedge portions 806 and 808 to one another.

The first wedge portion 806 can extend from the first end 802 to the second end 804. The first wedge portion 806 can have an upper surface 812 and a lower surface 814 that are opposite one another along a third direction $D_3$, perpendicular to the first and second directions $D_1$ and $D_2$. At least one of the upper surface 812 and the lower surface 814 can taper towards the other as it extends towards the second end 804. The first wedge portion 806 can include an outer surface 816. In embodiments in which the first wedge portion 806 is spaced from the second wedge portion 808, the first wedge portion 806 can include an inner surface 818 that is opposite the outer surface 816 along the second direction $D_2$.

The second wedge portion 808 can extend from the first end 802 to the second end 804. The second wedge portion 808 can have an upper surface 824 and a lower surface 826 that are opposite one another along the third direction $D_3$, perpendicular to the first and second directions $D_1$ and $D_2$. At least one of the upper surface 824 and the lower surface 826 can taper towards the other as it extends towards the second end 804. The second wedge portion 808 can include an outer surface 820. In embodiments in which the second wedge portion 808 is spaced from the first wedge portion 806, the second wedge portion 808 can include an inner surface 822 that is opposite the outer surface 820 along the second direction $D_2$.

The spacer 800 can include at least one stop that is configured to limit an insertion depth of the spacer 800 into the bone 300. For example, at least one of the first wedge portion 806 and the second wedge portion 808 can include such a stop (e.g., 812a, 814a, 824a, 826a). In some examples, each of the first and second wedge portions 806 and 808 can include such a stop. In some examples, at least one of the first and second wedge portions 806 and 808 can include a plurality, such as a pair, of such stops. In some examples, the spacer 800 can have at least one stop (e.g., 812a, 824a) that is configured to abut the first bone segment 300a and at least one stop (e.g., 814a, 826a) that is configured to abut the second bone segment 300b. FIGS. 42 to 49 show an embodiment that has four stops, however, it will be understood that the spacer 800 can have as few as one of the stops or any combination of two or more of the stops.

At least one of the upper surface 812 and the lower surface 814 of the first wedge portion 806 can include a stop that is configured to limit an insertion depth of the spacer 800 into the bone 300. For example, the upper surface 812 can include a stop 812a that is configured to limit translation of the spacer 800 into the bone 300 along the first direction $D_1$. The upper surface 812 can include a bone contacting region 812b and a non-bone contacting region 812c. The bone contacting region 812b can be between the non-bone-contacting region 812c and the second end 804. The non-bone-contacting region 812c can be between the first end 802 and the bone contacting region 812b. The bone contacting region 812b can be inwardly offset from the non-bone-contacting region 812c with respect to the third direction $D_3$. The stop 812a can extend from the bone contacting region 812b to the non-bone-contacting region 812c so as to define a shoulder that is configured to abut one of the first and second bone segments 300a and 300b of the bone 300 when the spacer 800 is received in the osteotomy cut 307 in the bone 300. The stop 812a can extend between the outer surface 816 and the inner surface 818. The stop 812a be contoured (e.g., curved or angled) as it extends along the second direction $D_2$ between the outer surface 816 and the inner surface 818 so as to conform to the one of the first and second bone segments 300a and 300b.

Additionally, or alternatively, the lower surface 814 of the first wedge portion 806 can include a stop 814a that is configured to limit translation of the spacer 800 into the bone 300 along the first direction $D_1$. For example, the lower surface 814 can include a stop 814a that is configured to limit translation of the spacer 800 into the bone 300 along the first direction $D_1$. The lower surface 814 can include a bone contacting region 814b and a non-bone-contacting region 814c. The bone contacting region 814b can be between the non-bone-contacting region 814c and the second end 804. The non-bone-contacting region 814c can be between the first end 802 and the bone contacting region 814b. The bone contacting region 814b can be inwardly offset from the non-bone contacting region 814c with respect to the third direction $D_3$. The stop 814a can extend from the bone contacting region 814b to the non-bone-contacting region 814c so as to define a shoulder that is configured to abut another one of the first and second bone segments 300a and 300b of the bone 300 when the spacer 800 is received in the osteotomy cut 307 in the bone 300. The stop 814a can extend between the outer surface 816 and the inner surface 818. The stop 814a be contoured (e.g., curved or angled) as it extends along the second direction $D_2$ between the outer surface 816 and the inner surface 818 so as to conform to the other one of the first and second bone segments 300a and 300b.

Additionally, or alternatively, the upper surface 824 of the second wedge portion 808 can include a stop 824a that is configured to limit translation of the spacer 800 into the bone 300 along the first direction $D_1$. The upper surface 824a can include a bone contacting region 824b and a non-bone-contacting region 824c. The bone contacting region 824b can be between the non-bone-contacting region 824c and the second end 804. The non-bone-contacting region 824c can be between the first end 802 and the bone contacting region 824b. The bone contacting region 824b can be inwardly offset from the non-bone-contacting region 824c with respect to the third direction $D_3$. The stop 824a can extend from the bone contacting region 824b to the non-bone-contacting region 824c so as to define a shoulder that is configured to abut the one of the first and second bone segments 300a and 300b of the bone 300 when the spacer 800 is received in the osteotomy cut 307 in the bone 300. The stop 824a can extend between the outer surface 820 and the inner surface 822. The stop 824a be contoured (e.g., curved or angled) as it extends along the second direction $D_2$ between the outer surface 820 and the inner surface 822 so as to conform to the one of the first and second bone segments 300a and 300b.

Additionally, or alternatively, the lower surface 826 of the second wedge portion 808 can include a stop 826a that is configured to limit translation of the spacer 800 into the bone 300 along the first direction $D_1$. For example, the lower surface 826 can include a stop 826a that is configured to limit translation of the spacer 800 into the bone 300 along the first direction $D_1$. The lower surface 826 can include a bone contacting region 826b and a non-bone-contacting region 826c. The bone contacting region 826b can be between the non-bone-contacting region 826c and the second end 804. The non-bone-contacting region 826c can be between the first end 802 and the bone contacting region 826b. The bone contacting region 826b can be inwardly offset from the non-bone-contacting region 826c with respect to the third direction $D_3$. The stop 826a can extend from the bone contacting region 826b to the non-bone-contacting region 826c so as to define a shoulder that is configured to abut the other one of the first and second bone segments 300a and 300b of the bone 300 when the spacer 800 is received in the osteotomy cut 307 in the bone 300. The stop 826a can extend between the outer surface 820 and the inner surface 822. The stop 826a be contoured (e.g., curved or angled) as it extends along the second direction $D_2$ between the outer surface 820 and the inner surface 822 so as to conform to the other one of the first and second bone segments 300a and 300b.

The first wedge portion 806 can have a first height $H_1$ from the bone contacting region 812b of the upper surface 812 to the bone contacting region 814b of the lower surface 814 along the third direction $D_3$. Similarly, the second wedge portion 808 can have a second height $H_2$ from the bone contacting region 824b of the upper surface 824 to the bone contacting region 826b of the lower surface 826 along the third direction $D_3$. In one embodiment, the first height $H_1$ can be different from the second height Hz. For example, the first height $H_1$ can be equal to the second height Hz such that the first and second wedge portions 806 and 808 provide the same spacing within the osteotomy cut 307. In such a case, the spacer 800 can be configured to correct a deformity in the frontal plane (i.e., planar adjustment of the first bone segment 300a). In another example, the first height $H_1$ can be less than or greater than the second height $H_2$ to provide different spacing within the osteotomy cut 307. In such a case, the spacer 800 can be configured to correct a deformity in both the frontal plane and the sagittal plane (i.e., bi-planar adjustment of the first bone segment 300a).

Figure 49:
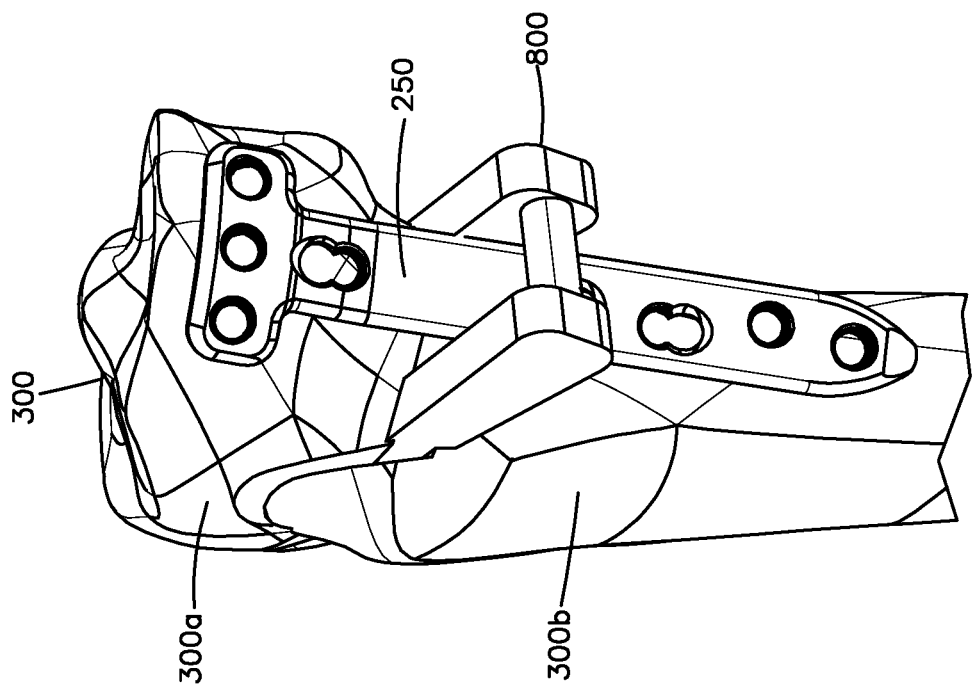
FIG. 49 shows the tibia and spacer of FIG. 42 with a bone fixation plate attached to the tibia.
Figure 48:
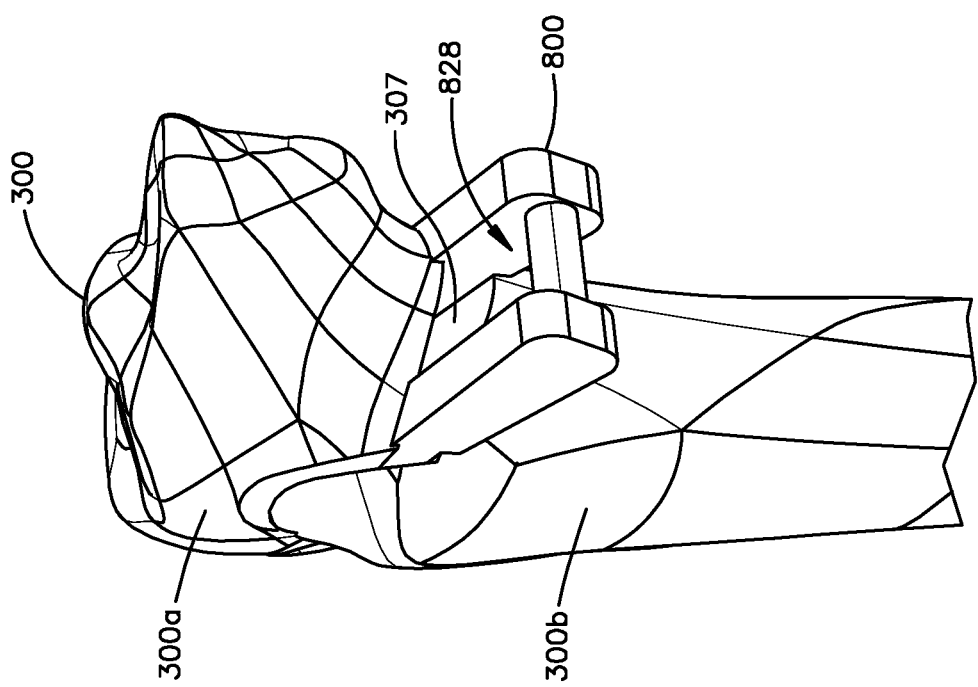
FIG. 48 shows a perspective view of a tibia with the spacer of FIG. 42 implanted into an osteotomy cut in the tibia.

The connector 810 can extend from the first wedge portion 806 to the second wedge portion 808 along the second direction $D_2$. The connector 810 can be supported by the first and second wedge portions 806 and 808 adjacent the first end 802. The connector 810 can be offset from each of the at least one stop towards the first end 802 with respect to the first direction $D_1$ such that a space 828 is defined between the at least one stop and the connector 810. As shown in FIGS. 48 and 49, the space 828 can be sized to receive the bone fixation plate 250 between the connector 810 and the bone 300 when the at least one stop abuts the bone 300.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

What is claimed:

1. An osteotomy guide configured to guide cutting of a bone, the osteotomy guide comprising:
   an anterior end and a posterior end that are spaced from one another along a transverse direction;
   an inner surface configured to face bone, and an outer surface opposite the inner surface along an outward direction, wherein each of the inner surface and the outer surface extends between the anterior end and the posterior end, and the inner surface defines:
   i) a first arm that includes a first bone contacting region; and
   ii) a second arm that is offset from the first arm with respect to the transverse direction and includes a second bone contacting region that is spaced from the first bone contacting region so as to define a gap therebetween that 1) extends from the first bone contacting region to the second bone contacting region, and 2) extends from the inner surface towards the outer surface along the outward direction, wherein the first and second arms are separated from one another by the gap;
   at least one transverse guide surface that extends between the outer surface and the inner surface, and is elongate along a transverse axis that extends along the transverse direction so as to at least partially define a transverse cutting path into the bone, wherein the at least one transverse guide surface is offset from the gap along a distal direction;
   at least one ascending guide surface that extends between the outer surface and the inner surface, and is oriented along an ascending axis that extends along an ascending direction so as to at least partially define an ascending cutting path into the bone; and
   first and second push tabs, wherein the second push tab is offset from the first push tab in each of the distal direction, the transverse direction, and the outward direction, and the second push tab is offset from the first push tab toward the ascending guide surface, such that a center of the second push tab is disposed between a center of the first push tab and the ascending axis with respect to the transverse direction.

2. The osteotomy guide of claim 1, wherein the first and second bone contacting regions are offset from one another along the transverse direction, and the second bone contacting region is offset from the first bone contacting region along the distal direction.

3. The osteotomy guide of claim 1, wherein the ascending direction is angularly offset from the distal direction and the transverse direction, the ascending axis and the transverse axis intersect one another, and wherein the at least one transverse guide surface extends beyond the at least one ascending guide surface with respect to the transverse direction.

4. The osteotomy guide of claim 1, wherein the ascending direction is angularly offset from the distal direction and the transverse direction, the ascending axis and the transverse axis intersect one another, and wherein the at least one transverse guide surface is intersected by a plane that is defined by the at least one ascending guide surface.

5. The osteotomy guide of claim 1, wherein the second arm includes an edge that is configured to abut the bone when the osteotomy guide is properly positioned along the bone, and the edge is configured to be viewed through the gap to verify that the edge abuts the bone and no space exists between the edge and the bone.

6. The osteotomy guide of claim 1, wherein the first push tab is configured to be pressed by a medical professional so as to properly align a position of the osteotomy guide along the distal direction, and a proximal direction opposite the distal direction.

7. The osteotomy guide of claim 6, wherein the second push tab is configured to be pressed by a medical professional so as to properly align a position of the osteotomy guide along the transverse direction.

8. The osteotomy guide of claim 3, further comprising a bridge that is disposed between the at least one transverse guide surface and the at least one ascending guide surface, such that the bridge is configured to obstruct a cut along the ascending cutting path at a location spaced from the transverse axis.

9. An osteotomy guide configured to guide cutting of a bone, the osteotomy guide comprising:
   an anterior end and a posterior end that are spaced from one another along a transverse direction;
   an inner surface configured to face the bone, and an outer surface that is opposite the inner surface, wherein at least a portion of the inner surface is contoured to face the bone;
   first and second transverse guide surfaces that face each other so as to define a transverse groove therebetween that is elongate along a transverse axis along the transverse direction so as to define a transverse cutting path, wherein the transverse groove has an open first end and a closed second end opposite the open first end; and first and second ascending guide surfaces that face each other so as to define an ascending groove therebetween that is elongate along an ascending axis along an ascending direction so as to define an ascending cutting path, wherein the ascending axis intersects the transverse groove, such that the ascending axis and the transverse axis intersect one another so as to define an oblique angle, wherein the transverse groove extends beyond the ascending groove in each of two opposite directions that extend along the transverse direction.

10. The osteotomy guide of claim 9, wherein the transverse groove is intersected by a plane that is defined by the ascending groove.

11. The osteotomy guide of claim 9, wherein the second arm includes an edge that is configured to abut the bone when the osteotomy guide is properly positioned along the bone, and the edge is configured to be viewed through the gap to verify that the edge abuts the bone and no space exists between the edge and the bone.

12. The osteotomy guide of claim 9, wherein:
1) the first push tab is configured to be pressed by a medical professional so as to align a position of the osteotomy guide on the bone along the distal direction, and a proximal direction opposite the distal direction, and
2) the second push tab is configured to be pressed by a medical professional so as to align a position of the osteotomy guide on the bone along the transverse direction.

13. The osteotomy guide of claim 9, wherein:
the osteotomy guide is configured to guide cutting of an osteotomy cut in the bone so as to divide the bone into a first bone segment and a second bone segment, the first bone segment defining an articular surface of the joint; and
the osteotomy guide includes an alignment guide that defines an opening therethrough that extends along the outer direction, the opening configured to receive an alignment member that projects into the osteotomy cut and abuts an inner surface of the second bone segment when the first bone segment is adjusted to a desired realignment.

14. The osteotomy guide of claim 9, further comprising a bridge that is disposed between the transverse groove and the ascending groove, wherein the bridge is configured to obstruct the ascending cutting path, such that a cut along the ascending groove terminates at a location spaced from the transverse axis.

15. An osteotomy guide configured to guide cutting of a bone, the osteotomy guide comprising:
an anterior end and a posterior end that are spaced from one another along a transverse direction;
an inner surface configured to face bone, and an outer surface opposite the inner surface along an outer direction, wherein each of the inner surface and the outer surface extends between the posterior end and the anterior end;
a first arm defining a first bone contacting region at the inner surface;
a second arm that is offset from the first arm with respect to the transverse direction and defines 1) a second bone contacting region at the inner surface that is spaced from the first bone contacting region so as to define a gap therebetween that extends from the inner surface towards the outer surface along the outer direction, and 2) a first push tab at the outer surface, wherein the first and second arms are separated from one another by the gap;
a second push tab at the outer surface, wherein the second push tab is offset from the first push tab in each of the distal direction, the transverse direction, and the outward direction;
a third bone contacting region that is disposed at the inner surface, extends between the first bone contacting region and the second bone contacting region, and at least partially defines the gap;
first and second transverse guide surfaces that extend between the outer surface and the inner surface, and face each other so as to define a transverse groove therebetween that is elongate along a transverse axis along the transverse direction so as to define a transverse cutting path into the bone; and
a bone fixation hole that extends through the inner surface and the outer surface, wherein the bone fixation hole is open to the transverse groove.

16. The osteotomy guide of claim 15, wherein the second arm includes an edge that is configured to abut the bone when the osteotomy guide is properly positioned along the bone, and the edge is configured to be viewed through the gap to verify that the edge abuts the bone and no space exists between the edge and the bone.

17. The osteotomy guide of claim 15, wherein
the first push tab is configured to be pressed by a medical professional so as to align a position of the osteotomy guide on the bone along the distal direction, and a proximal direction opposite the distal direction, and wherein
the second push tab is configured to be pressed by a medical professional so as to align a position of the osteotomy guide on the bone along the transverse direction.

18. The osteotomy guide of claim 15, further comprising:
first and second ascending guide surfaces that face each other so as to define an ascending groove therebetween that is elongate along an ascending axis along an ascending direction so as to define an ascending cutting path into the bone, wherein the ascending axis and the transverse axis intersect one another; and
a bridge that is disposed between the transverse groove and the ascending groove, wherein the bridge is configured to obstruct the ascending cutting path, such that a cut along the ascending groove terminates at a location spaced from the transverse axis.

* * * * *